US012251433B2

(12) United States Patent
Stentz et al.

(10) Patent No.: US 12,251,433 B2
(45) Date of Patent: *Mar. 18, 2025

(54) ENGINEERING GUT COMMENSAL BACTERIA TO EXPRESS HETEROLOGOUS PROTEINS IN THEIR OUTER MEMBRANE VESICLES (OMVS) FOR DELIVERY TO THE GI-TRACT

(71) Applicants: QUADRAM INSTITUTE BIOSCIENCE, Norwich (GB); UEA ENTERPRISES LIMITED, Norwich (GB)

(72) Inventors: Regis Gabriel Stentz, Norwich (GB); Simon Richard Carding, Norwich (GB)

(73) Assignees: QUADRAM INSTITUTE BIOSCIENCE, Norwich (GB); UEA ENTERPRISES LIMITED, Norwich (GB)

( * ) Notice: Subject to any disclaimer, the term of this patent is extended or adjusted under 35 U.S.C. 154(b) by 234 days.

This patent is subject to a terminal disclaimer.

(21) Appl. No.: 17/316,219

(22) Filed: May 10, 2021

(65) Prior Publication Data

US 2021/0268094 A1 Sep. 2, 2021

Related U.S. Application Data

(62) Division of application No. 16/086,906, filed as application No. PCT/GB2017/051199 on Apr. 28, 2017, now Pat. No. 11,000,581.

(30) Foreign Application Priority Data

Apr. 29, 2016 (GB) ..................................... 1607510

(51) Int. Cl.

| | |
|---|---|
| ***A61K 39/39*** | (2006.01) |
| ***A61K 35/74*** | (2015.01) |
| ***A61K 39/02*** | (2006.01) |
| ***A61K 39/112*** | (2006.01) |
| ***A61P 31/04*** | (2006.01) |
| ***C12N 1/20*** | (2006.01) |
| ***C12N 9/24*** | (2006.01) |
| ***C12N 15/52*** | (2006.01) |
| ***C12N 15/74*** | (2006.01) |
| ***C12P 21/02*** | (2006.01) |
| *A61K 38/00* | (2006.01) |
| *A61K 39/00* | (2006.01) |

(52) U.S. Cl.

CPC .......... *A61K 39/0216* (2013.01); *A61K 35/74* (2013.01); *A61K 39/0275* (2013.01); *A61P 31/04* (2018.01); *C12N 1/20* (2013.01); *C12N 9/2488* (2013.01); *C12N 15/52* (2013.01); *C12N 15/74* (2013.01); *C12P 21/02* (2013.01); *A61K 38/00* (2013.01); *A61K 2039/541* (2013.01); *A61K 2039/6068* (2013.01); *C07K 2319/02* (2013.01)

(58) Field of Classification Search

CPC .................................................. A61K 39/0216

See application file for complete search history.

(56) References Cited

U.S. PATENT DOCUMENTS

| | | | | |
|---|---|---|---|---|
| 11,000,581 | B2 * | 5/2021 | Stentz | A61P 31/04 |
| 11,766,461 | B2 * | 9/2023 | Sonnenburg | C12N 15/52<br>536/24.1 |
| 2017/0145061 | A1 * | 5/2017 | Lu | C07K 14/5428 |

* cited by examiner

*Primary Examiner* — Albert M Navarro

(74) *Attorney, Agent, or Firm* — Crowe & Dunlevy, P.C.

(57) ABSTRACT

This invention relates to the delivery of heterologous peptides or proteins such as therapeutic peptides, therapeutic proteins or antigens to mucosal sites using vesicles derived from the outer membrane of commensal bacteria, recombinant bacteria capable of producing such vesicles, and methods for the production of such vesicles. The invention further relates to an inducible expression system for use in recombinant bacteria.

13 Claims, 11 Drawing Sheets

Figure 1:
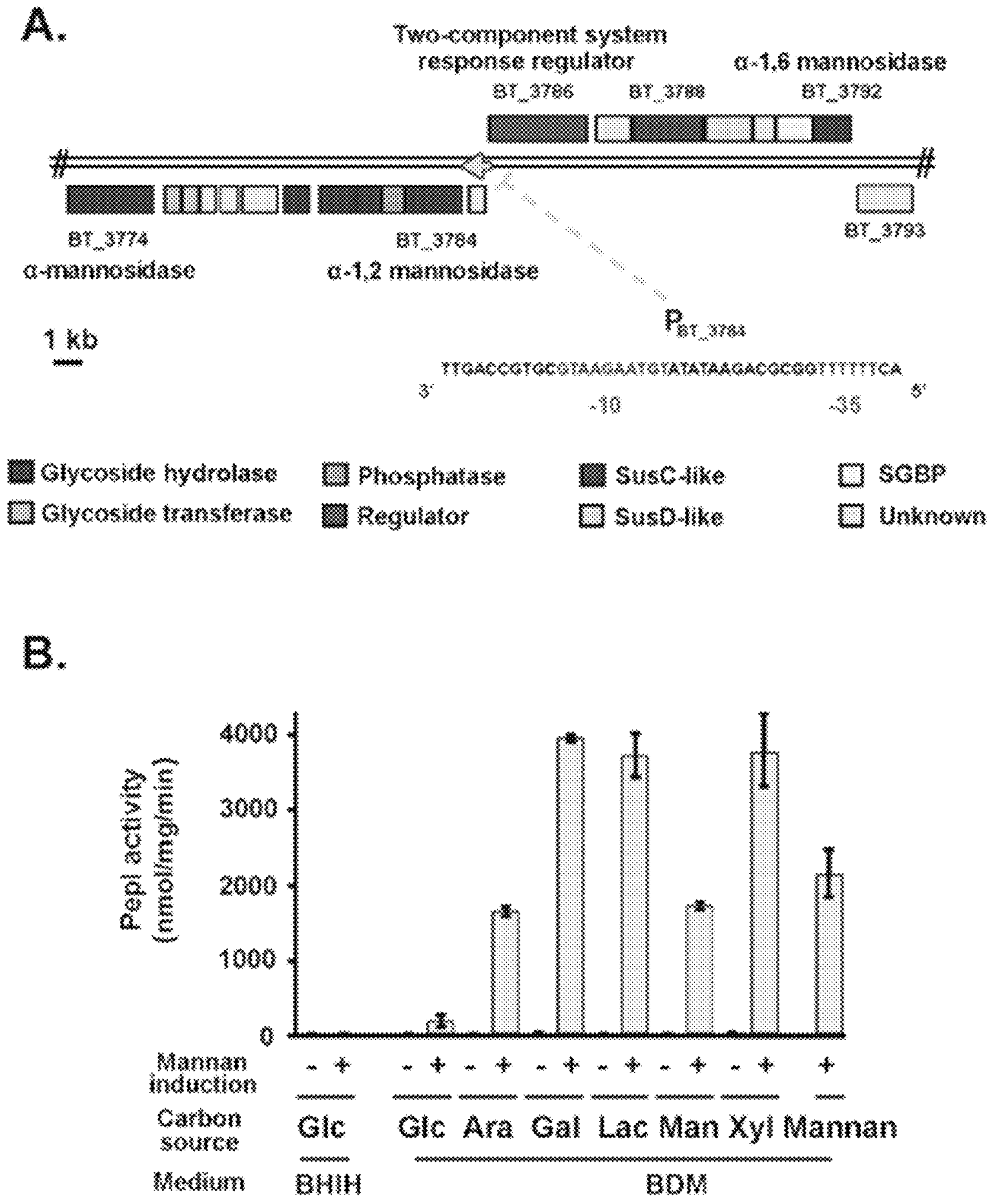

Specification includes a Sequence Listing.

GP2 (M cells) / UEA-1 (Globlet cells) / F-actin

Figure 10. Mannan-induced BtCepA expression increases the resistance of *B. thetaiotaomicron* to ampicillin

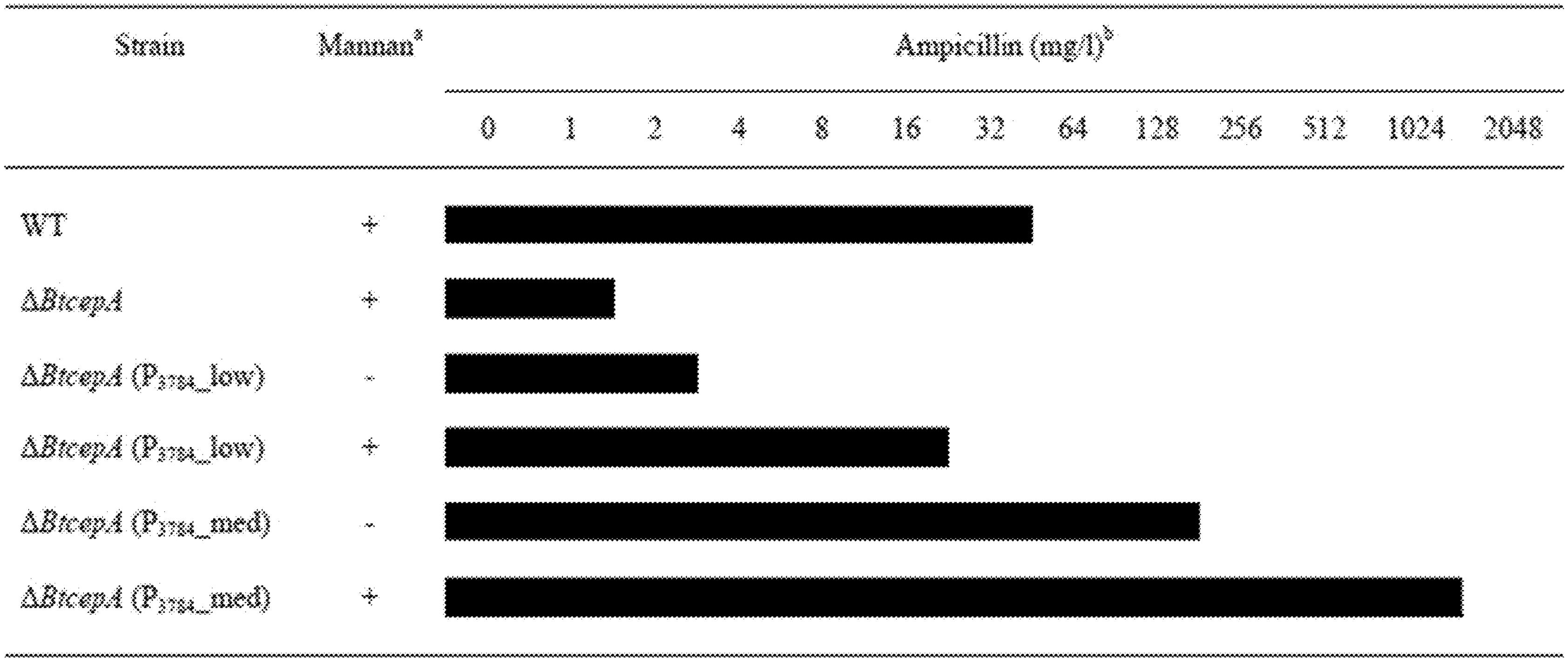

[a] Addition of 100 mg/l mannan to bacterial cultures with an $OD_{600}$ of 0.5 and the cells were incubated for 16 h

[b] Determination of ampicillin minimum inhibitory concentration (MIC) for the different *B. thetaiotaomicron* strains. The horizontal bars in black cover the ampicillin concentrations that permit growth for each of the strains. The results are representative of two independent experiments.

ENGINEERING GUT COMMENSAL BACTERIA TO EXPRESS HETEROLOGOUS PROTEINS IN THEIR OUTER MEMBRANE VESICLES (OMVS) FOR DELIVERY TO THE GI-TRACT

FIELD OF THE INVENTION

This invention relates to the delivery of heterologous peptides or proteins such as therapeutic peptides, therapeutic proteins or antigens to mucosal sites using vesicles derived from the outer membrane of commensal bacteria, recombinant bacteria capable of producing such vesicles, and methods for the production of such vesicles. The invention further relates to an inducible expression system for use in recombinant bacteria.

BACKGROUND OF THE INVENTION

Greater than 90% of infections occur in mucosal sites of the body although only a handful of mucosal vaccines are currently licensed including FluMist and NASOVAC (influenza virus), RotaTeq (rotavirus), Vivotif (*Salmonella typhi*) and Dukoral (*Vibrio cholera*) with the standout success being the oral polio vaccine. The limited availability of mucosal vaccines is principally related to the lack of effective delivery systems able to preserve vaccine antigen (Ag) integrity, and strong adjuvanticity.

Currently available vaccines are delivered by injection, with the associated problems of safety, patient compliance, morbidity and high cost. Injected vaccines also provide only partial or no protection at the (mucosal) sites of the body through which the vast majority (90%) of pathogens gain entry and in particular, via the gastrointestinal and respiratory tracts. The lack of effective vaccines is particularly acute in farming and in protecting against major enteric infections such as *Salmonella* and *Campylobacter*, which via contamination of the food supply is a major source and route of infection in humans. Further compounding the situation is increasing drug and antibiotic resistance that limits treatment options for intestinal infectious disease in both farm animals and humans, emphasizing the need to develop more effective vaccines.

Mucosal vaccination could overcome the major limitations of current injection-based vaccines and address the need for new vaccines to protect against gut infections. However, at present only a handful of mucosal (oral and nasal) vaccines are licensed. This limited availability is closely related to the lack of an effective delivery system able to preserve vaccine integrity particularly in the gut.

In the absence of effective treatments the incidence of intestinal infectious disease (IID) is increasing with 25% of the UK population suffering from an episode of IID each year resulting in 11 million days lost in people of working age. The impact of IID is also apparent in farming where the lack of effective vaccines for major enteric infections has serious consequences for livestock health and for food safety and protecting against food borne infections in humans, which is further compounded by increasing multi-drug and antibiotic resistance. Vaccination is an efficient and cost-effective form of preventing infectious disease although only a handful of mucosal vaccines are currently licensed, in large part due to a lack of effective mucosal vaccine delivery systems able to preserve antigen integrity during transit through the harsh environments of the upper GI tract.

Various controlled Ag release strategies have been developed for oral delivery including polymer microparticles, liposomes and immune-stimulating complexes that can require the inclusion of adjuvants to increase their immunogenicity. The complex manufacturing steps required to purify and encapsulate Ag into these particulate delivery systems can however render these approaches economically nonviable (Ulmer et al., 2006).

Another strategy is to exploit attenuated, avirulent pathogens that retain their invasiveness as vectors for oral delivery of vaccine Ag. Recombinant avirulent *Salmonella* vaccines have proven successful in providing protection against virulent forms of the pathogen in various model systems (Wang et al., 2013) although this promise has yet to be substantiated in human clinical trials. Also, the use of live attenuated pathogens in any vaccine formulation includes the risk of residual reversion and environmental contamination.

There therefore remains a need for improved antigen delivery systems.

The delivery of therapeutic peptides or proteins to mucosal sites by injection is similarly problematic. Delivery by injection negatively impacts cost, safety, patient compliance and also therefore treatment outcome. Furthermore, systemic delivery such as injection does not provide targeted delivery to mucosal sites for medical conditions where this is therapeutically advantageous. Oral or other non-invasive administration obviates the negative impact of injection, but presents other issues such as the potential for degradation of the peptide or protein by the proteolytic enzymes and acidic environment encountered in the digestive system. There therefore remains a need for improved delivery systems for therapeutic peptides or proteins.

SUMMARY OF THE INVENTION

In accordance with a first aspect, the invention provides a recombinant gram negative commensal gut bacterium comprising an expression system for expression of a therapeutic polypeptide or protein or an antigen in an outer membrane vesicle (OMV).

In another embodiment, the invention provides a recombinant gram negative commensal gut bacterium comprising an expression system for expression of any heterologous peptide or protein in an outer membrane vesicle (OMV). As used herein, the term "heterologous peptide or protein" means any length of chain of amino acids encoded by a nucleic acid sequence, and not normally present in the recombinant gram negative commensal gut bacterium; "heterologous peptide or protein" encompasses peptides, polypeptides and proteins.

Commensal gut bacteria are described in more detail herein and can include bacteria that are found in human or animal gut bacteria populations. In one embodiment of any aspect of the invention, the gram negative commensal gut bacterium is from the *Bacteroides* genus. In a further embodiment, the gram negative commensal gut bacterium is *Bacteroides thetaiotaomicron*. Examples of other species of gram negative commensal gut bacteria of the *Bacteroides* genus are provided herein.

Suitably, the expression system is one which facilitates stable expression of a therapeutic polypeptide or protein or an antigen in a gram negative commensal gut bacterium, for example, where the therapeutic polypeptide or protein or antigen sequence is integrated into the recombinant bacteria such that it is carried through to successive bacterial generations.

In one embodiment, the expression system comprises a therapeutic polypeptide or protein or an antigen sequence in a vector specific for the particular genus or strain of commensal gut bacteria, such as *Bacteroides*, wherein said therapeutic polypeptide or protein or antigen sequence is operably linked to a secretion signal sequence for targeting the antigen to the OMV. Suitably, the secretion signal sequence is OmpA, such as an OmpA sequence derived from *Bacteroides*. For example, where the *Bacteroides* is *Bacteroides thetaiotaomicron* (Bt), the OmpA sequence may be Bt OmpA. In one embodiment, the secretion signal sequence may be the N-terminal signal peptide of OmpA. In one embodiment, the recombinant bacteria incorporating the expression system is *Bacteroides thetaiotaomicron* (Bt). Other suitable signal peptides include BtMinpp and BtCepA. In another embodiment, the expression system comprises a heterologous peptide or protein fused to the N-terminal signal peptide of OmpA, preferably Bt OmpA. In one embodiment, the N-terminal signal peptide of OmpA is that of the gene BT_3852, the amino acid sequence of the N-terminal signal peptide of which is [SEQ ID NO. 1]: MKKILMLLAFAGVASVASA.

In one embodiment of the invention, the expression system in the recombinant gram negative commensal gut bacterium comprises an constitutive expression system, meaning an expression system comprising a constitutive promoter, such as for example the P1 promoter. Examples of such an expression system are exemplified herein.

In one embodiment of the invention, the expression system in the recombinant gram negative commensal gut bacterium comprises an inducible gene expression system, preferably a mannan-controlled gene expression system. Suitable inducible gene expression systems and constructs are familiar to those skilled in the art. In one embodiment the expression system in the recombinant gram negative commensal gut bacterium comprises a mannan-inducible promoter region of an alpha-1,2-mannosidase gene, at least one ribosomal binding site, a multiple cloning site and a transcriptional terminator.

In one embodiment, the antigen is derived from a pathogen or is suitable for generating an immune response against a particular pathogen. Suitable antigens are described in more detail herein.

In another embodiment, the therapeutic polypeptide or protein is one which can provide a therapeutic effect in an individual. Suitable therapeutic polypeptides or proteins are known to those skilled in the art and described in more detail herein.

Advantageously the OMV from *Bacteroides*, such as Bt, are highly stable.

In one embodiment, the OMV produced from the recombinant bacteria are in the range of approximately <50-300 nm in size.

In another aspect of the invention there is provided a method for preparing an outer membrane vesicle (OMV) containing a heterologous peptide or protein, comprising generating a recombinant gram negative commensal gut bacterium that expresses a heterologous peptide or protein in its OMV, cultivating the bacterium under conditions that result in the expression of said heterologous peptide or protein and the production of OMV, and isolating OMV thereby containing said heterologous peptide or protein. In another aspect of the invention there is provided a method for preparing an outer membrane vesicle (OMV) for use as a vaccine comprising generating a gram negative commensal gut bacterium that expresses an antigen in its OMV, cultivating the bacteria under conditions for producing OMVs and isolating said OMVs containing an antigen. In another aspect, there is provided a method for preparing an OMV for use as a therapeutic comprising generating a gram negative commensal gut bacterium that expresses a therapeutic polypeptide or protein in its OMV, cultivating the bacteria under conditions for producing OMVs and isolating said OMVs containing a therapeutic polypeptide or protein. Suitably the commensal gut bacteria are modified to express the heterologous peptide or protein or therapeutic polypeptide or protein or antigen of interest. Suitable methods for introducing nucleic acid molecules into bacteria for expression of peptides/polypeptides are known and include those methods described herein. In particular, the methods described herein exemplify how a nucleic acid encoding an antigen of interest may be introduced into a gram negative commensal gut bacteria such that the antigen expression is such that it is packaged into the OMV. These methods are equally applicable to a therapeutic polypeptide or protein. The methods described herein exemplify how a nucleic acid encoding a therapeutic protein of interest may be introduced into a gram negative commensal gut bacteria such that the therapeutic protein is packaged into the OMV.

The antigen is preferably a vaccine antigen i.e. an antigen against which an immune response is desired through vaccination. Suitable antigens for use as vaccine antigens are described herein.

Suitably, the gram negative commensal gut bacteria is *Bacteroides thetaiotaomicron* (Bt). In one embodiment, the OMV harvesting is carried out at a late stage of bacterial growth.

In one embodiment, the therapeutic polypeptide or protein or antigen may be expressed in the gram negative commensal gut bacterium using an inducible expression system. Advantageously, inducible expression may allow expression to be controlled such that it is optimally expressed for OMV packaging. In one embodiment, the method for preparing an OMV in accordance with the invention may use a mannan-inducible expression system as described herein. Advantageously OMVs are known to be mainly produced at a late stage of growth and a mannan-inducible system, as described herein allows delaying the expression of recombinant proteins, thus avoiding early expression of proteins that are potentially toxic to the cells. In one embodiment, expression of a heterologous peptide or protein is delayed until the stage of OMV production. In another embodiment, expression of a heterologous peptide or protein is tuned, or regulated, by varying the concentration of an inducing composition. An inducing composition means any composition which when provided to the recombinant gram negative commensal gut bacterium results in induction, expression or upregulation of a gene encoded by the expression system. For example, when the expression system comprises a mannan-inducible expression system in accordance with the invention, expression of a heterologous peptide or protein may be tuned by varying the concentration of mannan. By selecting an appropriate concentration of the inducing composition, the level of expression of the heterologous peptide or protein may be tuned such that it, for example, remains below a toxic threshold. Suitable concentrations, and methods of selecting an appropriate concentration, of the inducing composition are described herein.

In another aspect of the invention, there is provided an OMV from a recombinant gram negative commensal gut bacterium comprising an expression system for expression of a heterologous peptide or protein. In another aspect there is provided an OMV containing a heterologous peptide or protein produced according to the methods of the invention.

In another aspect there is a provided an OMV containing a heterologous peptide or protein for use as a medicament.

In another aspect the OMV containing a heterologous peptide or protein may be used in the treatment of inflammatory gut disease. Examples of inflammatory gut diseases will be known to those skilled in the art and are exemplified herein. In another aspect there is provided an OMV containing a heterologous peptide or protein for use as a vaccine. In another aspect of the invention, there is provided an antigen-containing OMV for use as a medicament. In another aspect, there is provided an OMV containing a therapeutic polypeptide or protein for use as a medicament. Suitably the OMV is produced from a recombinant commensal bacteria which comprises an expression system for expressing a heterologous peptide or protein, a therapeutic polypeptide or protein or an antigen in accordance with any aspect of the invention. In one embodiment, the antigen-containing OMV is for use as a vaccine and, in particular, for use as a vaccine that can be administered to the mucosal surfaces in a human or animal. Accordingly, there is provided an antigen-containing OMV for mucosal delivery, such as enteral administration e.g. oral (as tablets, capsules or drops), intranasal (as drops, spray). Likewise, an OMV containing a therapeutic polypeptide or protein, or an OMV containing a heterologous peptide or protein, may be suitable for mucosal delivery and administration.

In one embodiment administration of an antigen-containing OMV in accordance with the invention generates protective immunity against a pathogen. Suitably, an adaptive immune response may be generated. For example, an antibody (IgG/IgA) and/or CD4 T cell response may be generated to a particular pathogen.

In another aspect, the invention provides a pharmaceutical composition comprising an OMV isolated from a recombinant bacteria in accordance with any aspect or embodiment of the invention. In one embodiment, a pharmaceutical composition may further comprise a pharmaceutically acceptable excipient. Suitably such an excipient will be one which allows the OMV structure to be retained or stabilised for mucosal administration. In another embodiment, the pharmaceutical composition may further comprise an adjuvant.

In one embodiment of any aspect of the invention, an antigen-containing OMV may be provided as a vaccine for use in humans or it may be provided for animal use. For example, an antigen-containing OMV in accordance with the invention may be for vaccination of farm animals such as pigs and chickens, thus providing a route to control against enteric infections such as *Salmonella* and *Campylobacter* by providing protective immunity. In another embodiment, use in humans may provide protection against major enteric infections such as norovirus.

In one embodiment of any aspect of the invention, an OMV containing a therapeutic peptide or protein may be provided as a therapeutic for use in humans or it may be provided for animal use. An OMV containing a therapeutic peptide or protein in accordance with the invention, for example KGF-2, may be used as a therapeutic for treatment of colitis in humans or for treatment of colitis in animals.

In another aspect of the invention there is provided an inducible gene expression system. Suitably, such an expression system may be used in a recombinant gram negative commensal gut bacterium of the *Bacteroides* genus. In one embodiment, an inducible gene expression system in accordance with the invention comprises:

- an inducible promoter region of a *Bacteroides*-encoded gene;
- at least one ribosomal binding site;
- a multiple cloning site; and
- a transcriptional terminator.

In another aspect of the invention there is provided a mannan-controlled gene expression system. Such an expression system may also be described as, for example, a mannan-inducible gene expression system, a mannan-inducible expression system or a mannan-inducible system. Suitably such an expression system may be used in a gram negative gut commensal bacteria, such as a *Bacteroides*. In a particular embodiment, the expression system may be used in *Bacteroides thetaiotaomicron*. Such an expression system may be particularly suitable for use in generating an antigen-containing OMV for use as a vaccine for mucosal immunisation. Likewise, such an expression system may be particularly suitable for use in generating an OMV containing a therapeutic polypeptide or protein.

In one embodiment, a mannan-controlled gene expression system in accordance with the invention comprises:

- a mannan-inducible promoter region of an alpha-1,2-mannosidase gene;
- a ribosomal binding site;
- a multiple cloning site; and
- a transcriptional terminator.

In one embodiment, the mannan-inducible promoter region is derived from the promoter identified for the gene BT_3784. In particular, the mannan-inducible promoter region may be derived from the P3784 promoter region sequence [SEQ ID NO. 2]:

```
5'-AATGTTTTTTCATGGCATAGAATCCTTAGATTTGCAATATGACAAA

GGTAAACAAAAAAACTTTCCAGCACTTTTTTGGCGCAGAATATATGTAA

GAATGCGTGCCAGTTTGGTTAATTATAGCGCCACAGGGCGATTTAGTGT

TTCGACTTCCGGTAGCGGCATTCCTTTTCTCTCTATTTTCGTCACAGAA

ACTAATTTTATTCATAAATTCATTTGTTCATGAAAACACATTTTTCATT

TAAACACCTGTTATTTATTGGAGGTGCGGT-3'.
```

Suitably, the mannan-inducible promoter region comprises the nucleic acid sequence

```
[SEQ ID NO. 3]:
5'-ACTTTTTTGGCGCAGAATATATGTAAGAATGCGTGCCAGTT-3'.
```

In another embodiment, the ribosomal binding site is one which is designed to modulate expression, while the multiple cloning site facilitates cloning of genes of interest. Examples of the different components of such a system are given in the Examples section herein.

In other embodiments, the inducible gene expression system in accordance with any aspect of the invention comprises a second ribosomal binding site. The choice of one, two, or more ribosomal binding sites permits the expression level of the heterologous peptide or protein to be varied.

In another embodiment, the invention provides a gene expression system in accordance with the invention wherein said gene expression system is for use in a recombinant bacteria for the production of OMV, in accordance with any aspect or embodiment of the invention.

In other embodiments, a mannan-inducible gene expression system in accordance with the invention can be used in any *Bacteroides*-derived expression system for production of proteins or products or in the study of *Bacteroides* physiology.

In other embodiments of the invention, an alternative *Bacteroides* inducible promoter such as one from e.g. *B. acidifaciens, B. caccae, B. coprocola, B. coprosuis, B. eggerthii, B. finegoldii, B. fragilis, B. helcogenes, B. intestinalis, B. massiliensis, B. nordii, B. ovatus, B. thetaiotaomicron, B. vulgatus, B. plebeius, B. uniformis, B. salyersai, B. pyogenes, B. goldsteinii, B. dorei* or *B. johnsonii* can be used to replace the mannan-inducible promoter from *B. thetaiotaomicron* in the expression vector. This is advantageous because the expression system can therefore function in other *Bacteroides* species.

FIGURES

FIG. 1. The MAN-PUL2 region and use of the P3784 promoter for mannan-induced expression of the pepI reporter gene. A) Genetic map of the *B. thetaiotaomicron* Group 2 PUL BT3774-92. Genes with known or predicted functions (according to Cuskin et al., (2015) and Xu et al., (2003)) are colour coded and genes with unknown function are represented in grey. SGBP; surface glycan binding protein. The sequence and orientation of the P3784 promoter are indicated. B) Expression of pepI under the control of P3784 in the presence of different carbon sources. The *B. thetaiotaomicron* strain GH193 containing the pepI gene under the dependence of the P3784 promoter was grown in the BHI complex medium to which hemin was added (BHIH). BHI is commercially supplied and contains 0.2% glucose. GH193 was also grown in minimal medium (BDMA) on different carbon sources (0.5%) to which 50 mg/L mannan (extracted from *S. cerevisiae*) was added where indicated.

Figure 2:
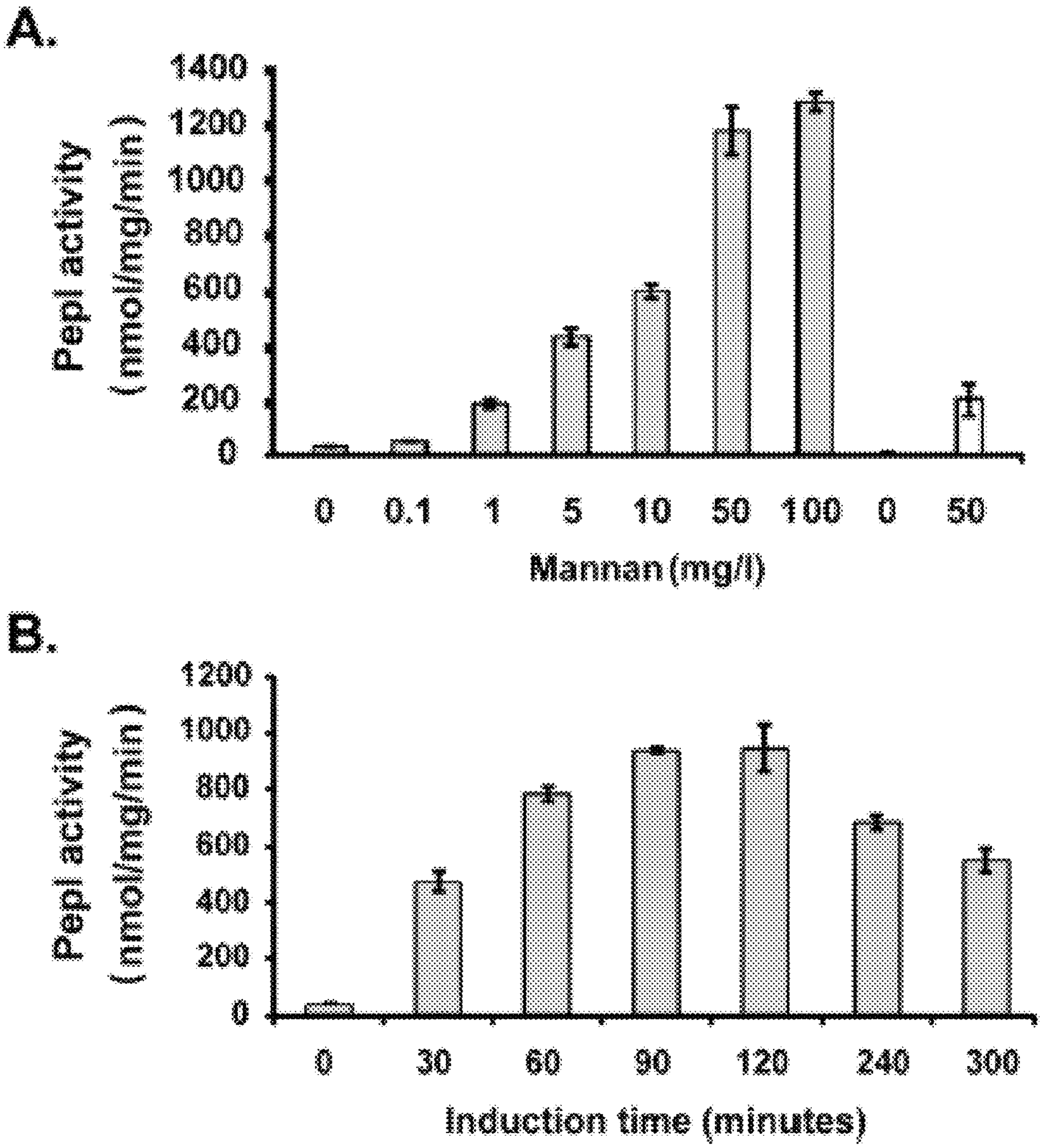

FIG. 2. Determination of optimal conditions for mannan-induced gene expression. A) The *B. thetaiotaomicron* strain GH193 (light grey) which expresses medium-levels of PepI under the control of the P3784 promoter was incubated in the presence of increasing concentrations of mannan and the specific activity of PepI was determined. The GH287 strain (white) contained a vector designed for low expression levels of PepI. B) GH193 was grown in the presence of mannan (100 mg/1) and PepI activity was measured in protein extracts from samples collected at different time points post induction.

Figure 3:
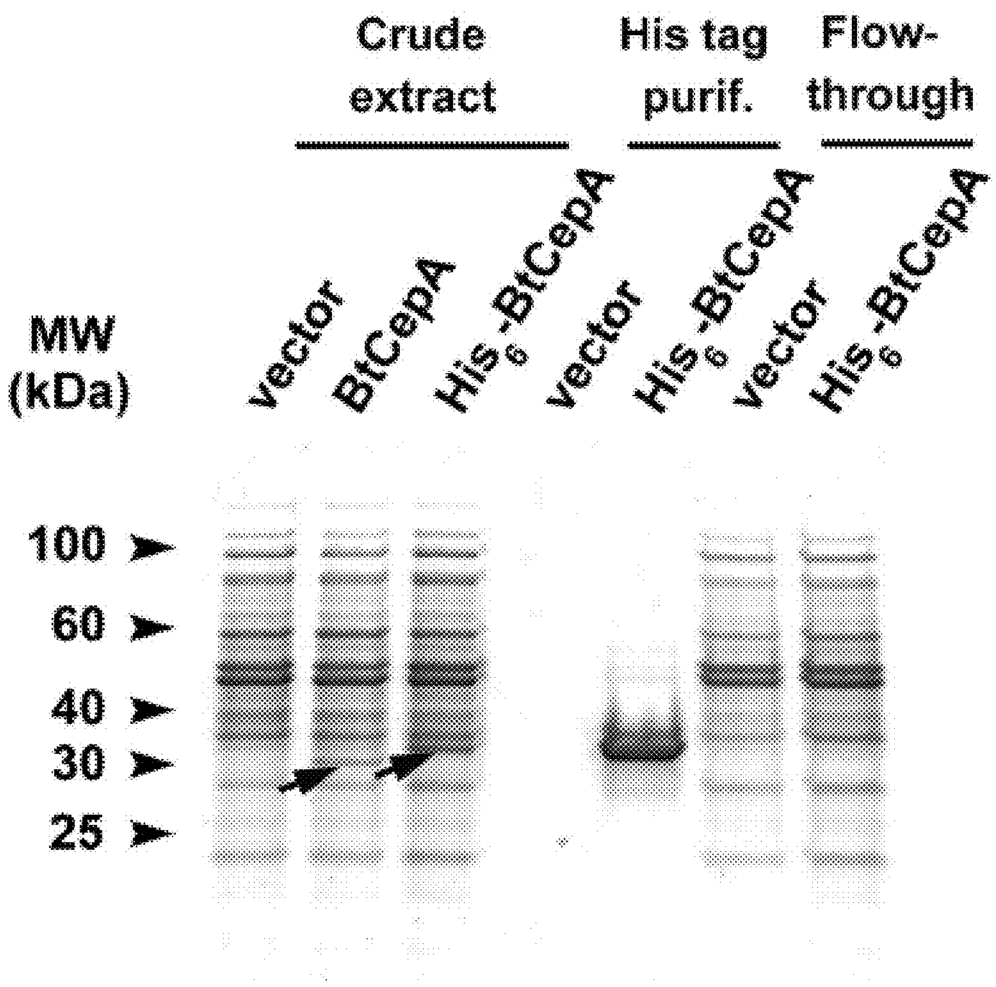

FIG. 3. SDS-PAGE of periplasmic protein extracts before and after Ni-NTA affinity chromatography. L: protein ladder; vector: extract from GH359 strain which contains the empty vector; BtCepA: extract from GH364 which expresses the native BtCepA; BtCepA-His6: extract from GH402 which expresses the C-terminally His-tagged 464 BtCepA. Flow-through was collected during the binding step of purification. The arrows indicate the bands corresponding to the native BtCepA and the higher molecular weight BtCepA [His]6.

Figure 4:
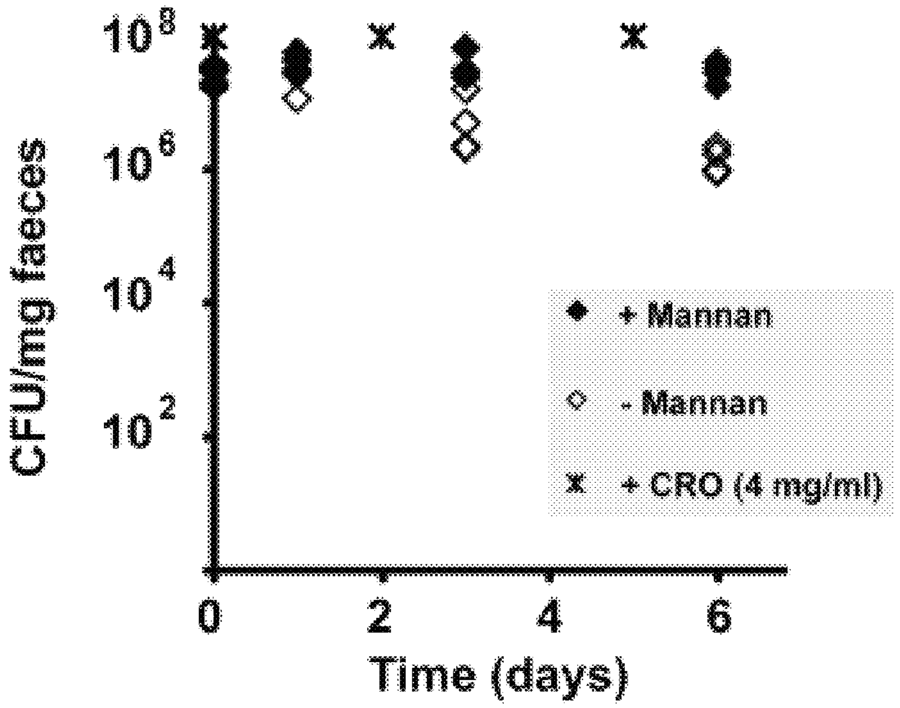

FIG. 4. In vivo induction of ceftriaxone resistance using exogenous α-mannan. Crosses indicate times of i.p. injections. GA: Group A of mice received mannan in their drinking water. GB: Group B of mice which were given access to regular drinking water. CRO: ceftriaxome.

Figure 5:
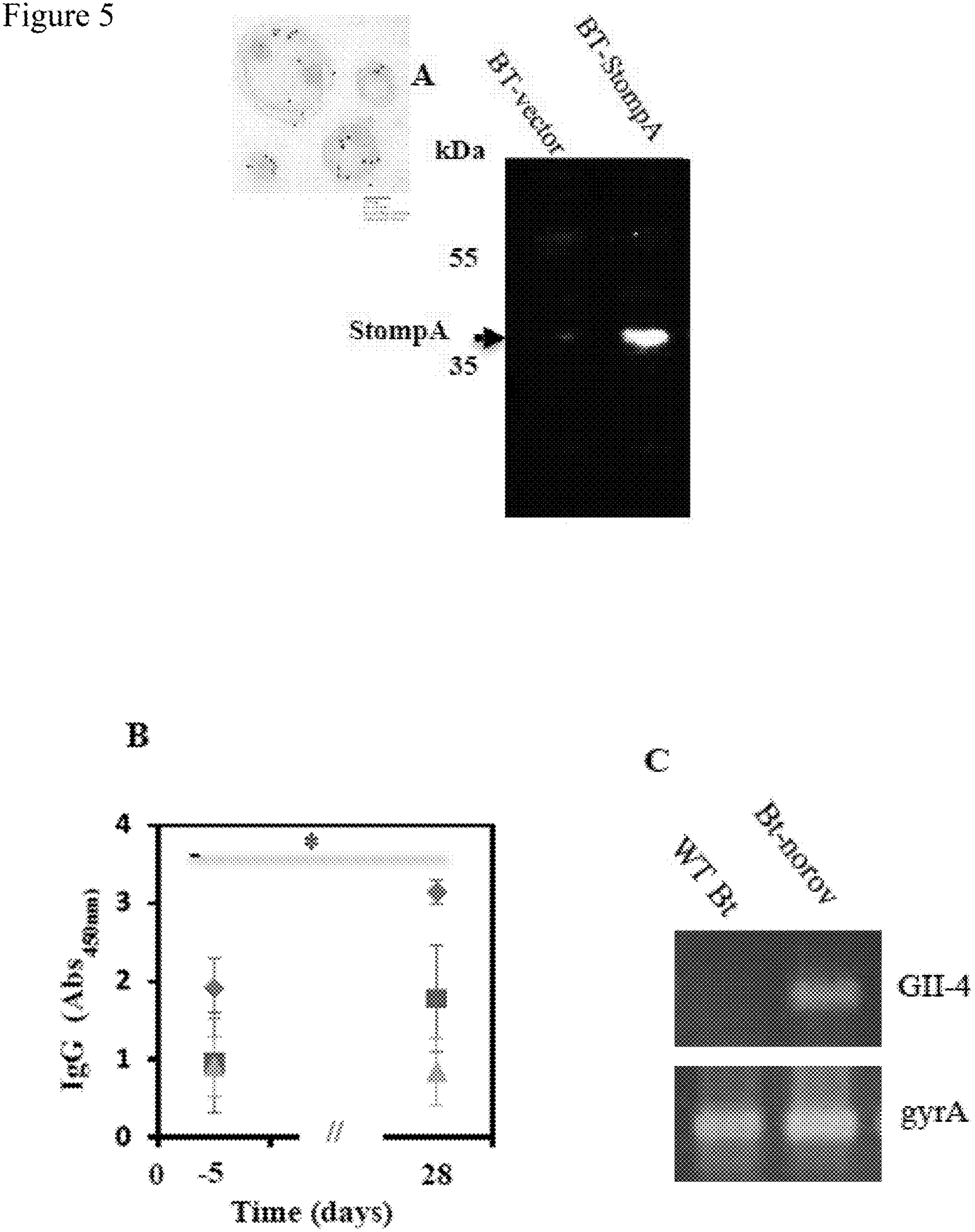

FIG. 5. Engineering Bt to express vaccine antigens. A) Expression of *Salmonella* OmpA (StompA) in Bt-OMVs detected by D3 of OMV lysates (arrow). Inset: ultrathin sections of Bt StompA+ OMVs stained with rabbit anti-StompA and anti-rabbit Ig-gold particles and imaged by EM. B) Levels of anti-StompA IgG in sera of mice (n=6ea.) 28 days post oral gavage with StompA+ Bt OMVs (squares) or wildtype Bt OMVs (triangles) or, after i.p. injection of StompA+ Bt OMVs (diamonds) determined by solid-phase ELISA. *$p<0.05$ comparing IgG levels pre-versus post oral and i.p. StompA+ OMV immunization. C) Expression of norovirus GII-4 capsid mRNA in recombinant Bt (norov) detected by RT-PCR. The gyrA gene was used as a control.

Figure 6:
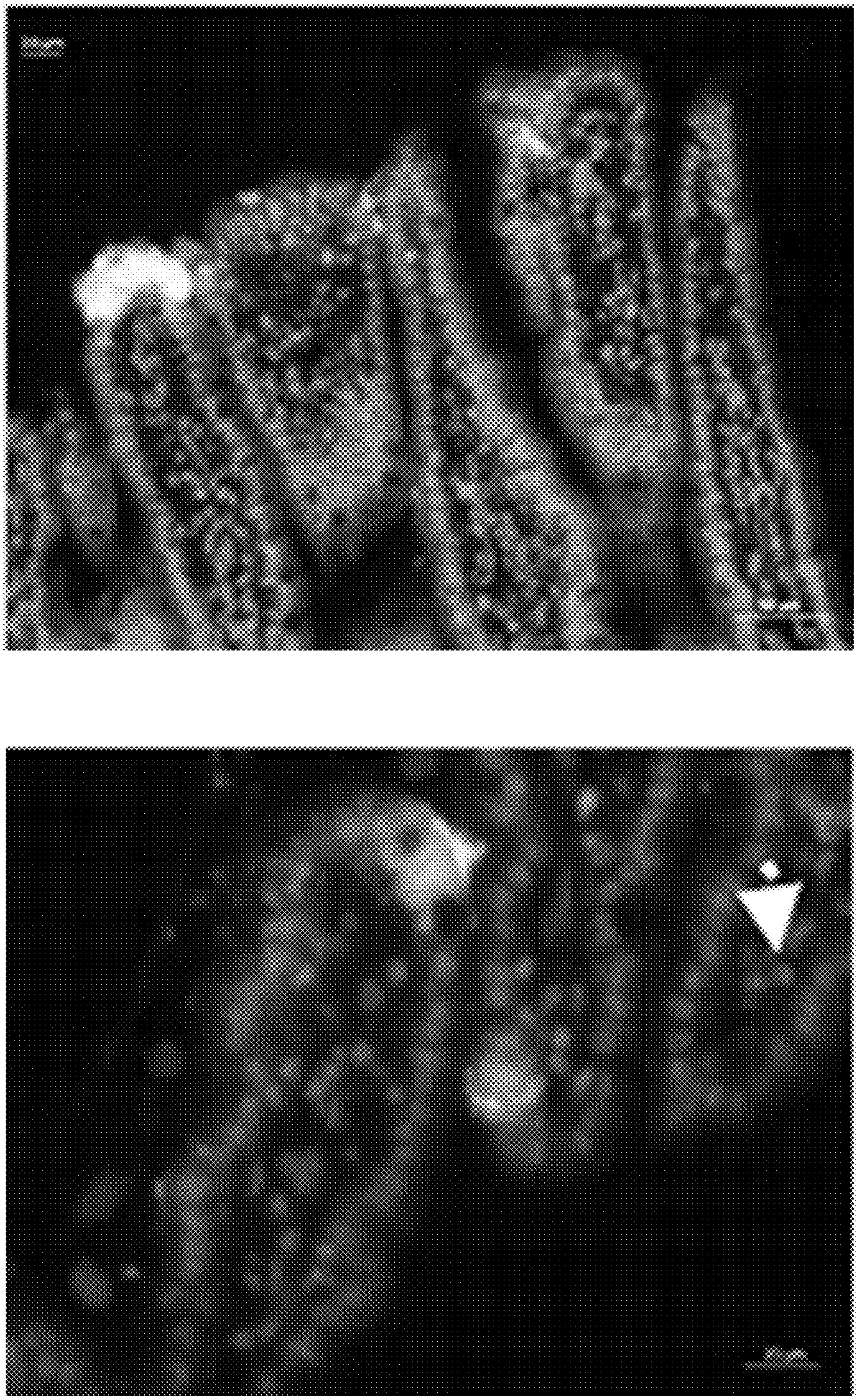

FIG. 6. Bt OMV-epithelium interactions in vivo. DiL-labelled OMVs (red) were injected into murine ileal loops and 30 min later tissues were snap frozen, sectioned (4 μm), counterstained with DAPI (blue) and imaged by UV microscopy (Zeiss Axiovert). The merged low (top) and high power (bottom) images show co-localisation (bright areas) of OMVs (aggregates) along the crypt villous axis and villus tips. The arrow identifies OMVs that may be located within the lamina propria.

Figure 7:
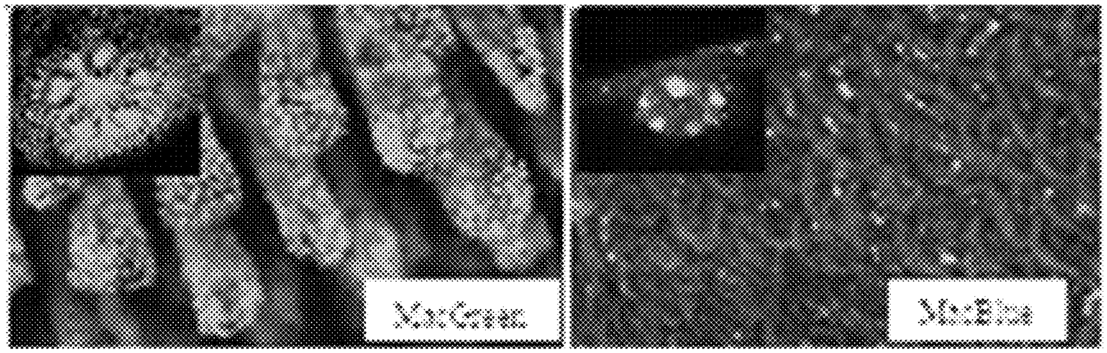
Figure 7:
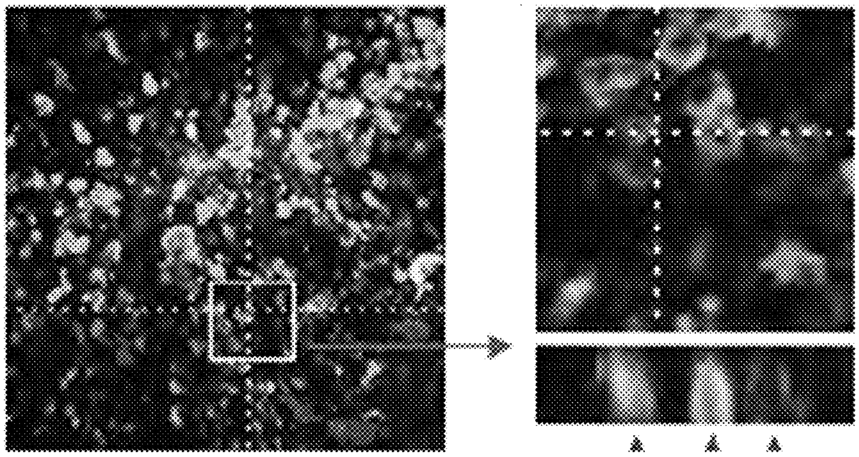

FIG. 7. Visualisation of DC/macrophages in whole tissue mounts of small intestine from Csf1r-EGF (Mac Green) and -ECF (Mac Blue) transgenic mice visualised by uv microscopy. The punctate staining in Mac Green tissue identifies abundant DC/macs in the villi whereas staining in the Mac Blue tissue shows the DC/macs in the subepithelial domes of isolated lymphoid follicles and their virtual absence in the villi. Insets: Staining of DC/macs in PP. The bottom right panel depicts whole-mount immunofluorescence detection of M cells (GP2+ cells; green) and goblet cells (UEA-1+ cells, red) in the FAE of a mouse Peyer's patch. Note the presence of the basolateral pockets beneath the M cells in the Z-projections (arrows) in the bottom right-hand panel.

Figure 8:
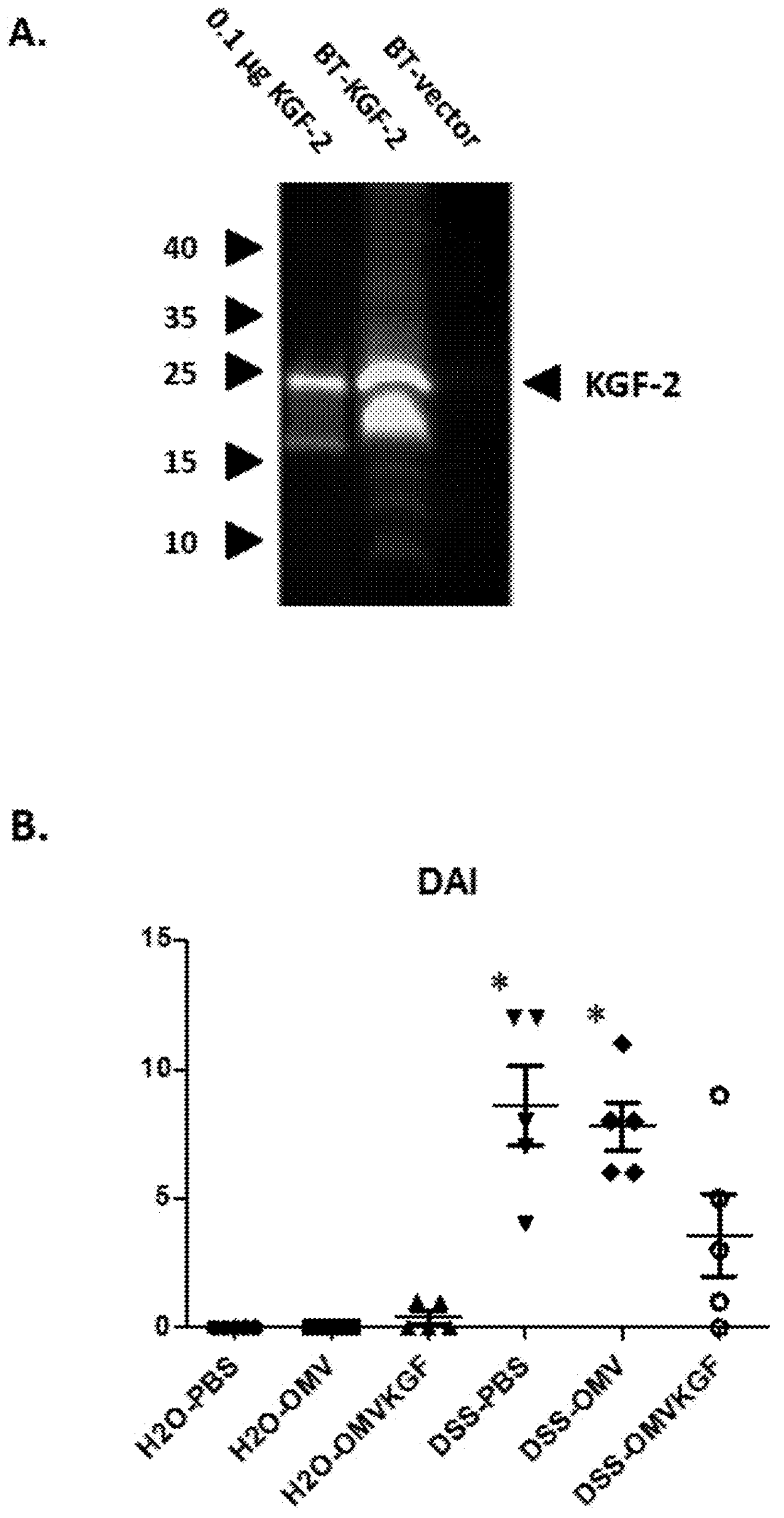
Figure 8:
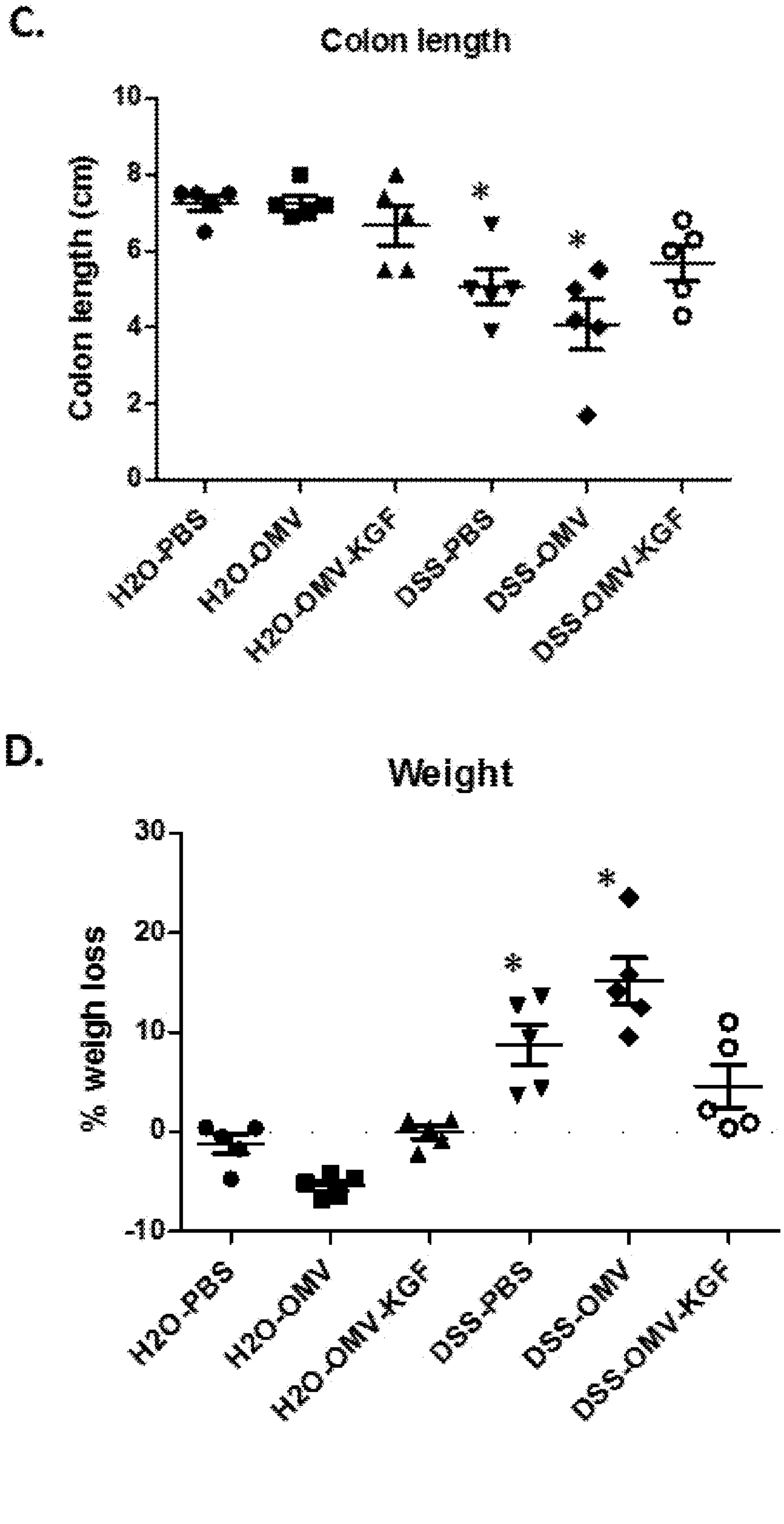

FIG. 8. Therapeutic effect of OMV-KGF-2 treatment of DSS-induced experimental colitis in mice. A) Engineering Bt to express and secrete the recombinant human keratinocyte growth factor-2 (KGF-2) in OMVs. Expression of KGF-2 fused to the N-terminal signal peptide of OmpA of Bt (BT_3852). The protein is detected by D3 of OMV lysates (arrow) using goat anti-KGF polyclonal antibodies. B) Disease activity index (DAI) scores were based on cumulative scores for weight loss, colon content consistency and colon content blood and appearance of caecum and colon tissue presented at day 7. DSS was administered to adult mice via drinking water for 7 days (2.5% DSS). At day 1, 3 and 5 mice were gavaged with PBS (DSS-PBS), control OMVs (DSS-OMV) and OMVs containing KGF-2 (DSS-OMVKGF). Control groups received PBS (H2O-PBS), control OMV (H2O OMV) or OMV containing KGF-2 (H2O-OMVKGF) C) Colonic length was measured from the ileocaecal junction to the anal verge at necropsy. D) Body weight loss was calculated as the percentage of the weight at day 7 over day 0.

*$p<0.05$ significantly different from the control group receiving the same treatment (PBS, OMV or OMV-KGF) (One way Anova).

Figure 9:
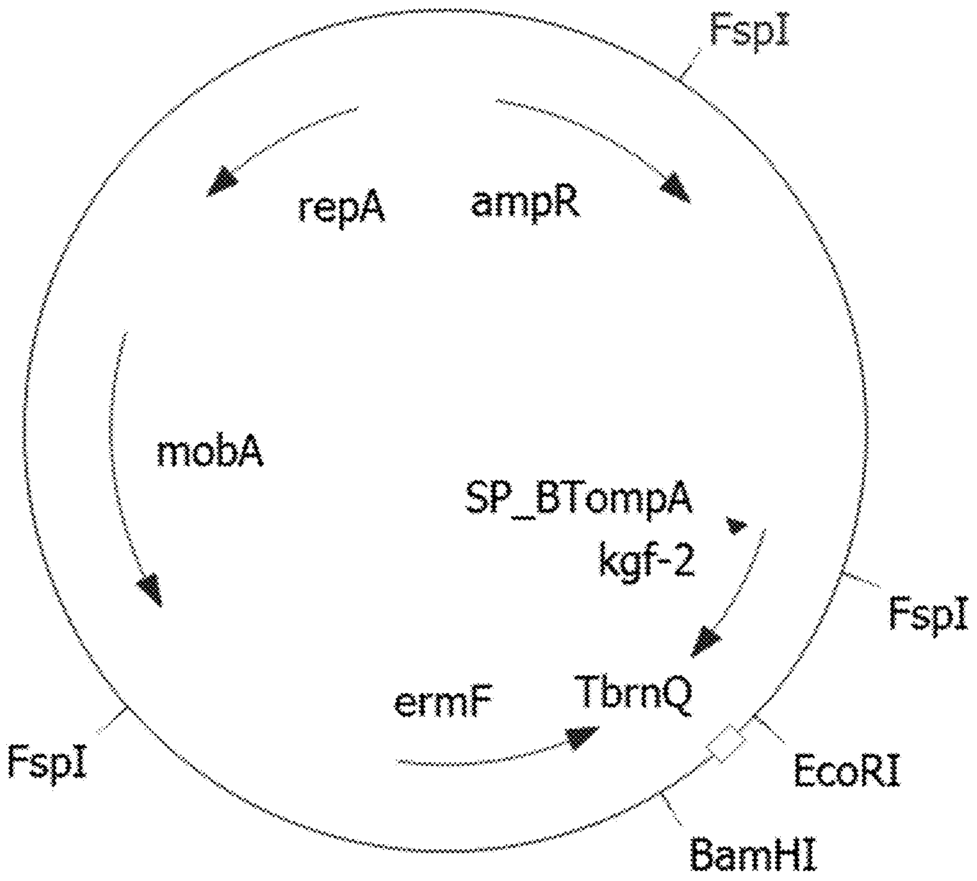

FIG. 9. Map of plasmid pGH173.

FIG. 10. Graphical representation of Mannan-induced BtCepA expression increases the resistance of *B. thetaiotaomicron* to ampicillin.

DETAILED DESCRIPTION OF INVENTION

The use of acellular membrane vesicles for Ag delivery can overcome biosafety concerns that have been reported for previous strategies for mucosal vaccination using attenuated, avirulent pathogens that retain their invasiveness as vectors for oral delivery of vaccine.

The present invention describes OMV technology based upon the Gram negative commensal gut bacterium, exemplified by *Bacteroides thetaiotaomicron* (Bt), that is engineered to express candidate vaccine antigens in their OMVs for mucosal delivery and generation of protective immunity against major animal pathogens.

OMV based vaccines offer significant advantages over conventional vaccines, (1) they are non-replicating, (2) oral and intranasal delivery overcomes the need for needles and they target mucosal sites, (3) they have an established safety record, (4) can elicit innate and Ag-specific adaptive immune responses, (5) possess self-adjuvant properties (i.e. MAMPs such as LPS), (6) are relatively cheap, quick and straightforward to produce and, (7) can be delivered outside a formal clinic setting. The limitations of current (pathogen-derived) OMV vaccines are the potential for unintended toxicity (due to associated toxins), low expression levels of protective Ags, variable efficacy depending on source and formulation, possible need for exogenous adjuvants, and provision of incomplete protection due to strain variation. These limitations can in principle be overcome through the use of non-pathogenic OMV-producing commensal (gut) bacteria and genetic engineering to improve their vaccine application.

The technology can in principle be used to deliver a range of vaccine antigens to mucosal sites to protect against various bacterial, viral and possibly parasitic diseases for food and companion animals and at risk human populations for which there are currently no effective mucosal vaccines.

Bt-OMVs have been shown to access and influence intestinal host cell physiology (Stentz et al., 2014) and activate mucosal immune cells in vivo (Kaparakis-Liaskos et al., 2015 and Hickey et al., 2015) thus identifying a means by which gut bacteria influence intestinal homeostasis.

Gram Negative Commensal Bacteria

A wide range of commensal bacteria are known in both humans and animals. In the context of the present invention, relating to mucosal delivery, bacteria that are naturally found along the mucosal linings e.g. gut, respiratory tract etc. may be of particular use.

*Bacteroides* are highly represented among the commensal gut bacteria in humans. Reference to *Bacteroides*, as used herein, is to the genus of gram-negative, obligate anaerobic bacteria. Species from the genus *Bacteroides* are non-endospore-forming bacilli, which may be either motile or non-motile, depending on the species: *Bacteroides* membranes contain sphingolipids and meso-diaminopimelic acid in their peptidoglycan layer.

Species of *Bacteroides* include *B. acidifaciens, B. caccae, B. coprocola, B. coprosuis, B. eggerthii, B. finegoldii, B. fragilis, B. helcogenes, B. intestinalis, B. massiliensis, B. nordii, B. ovatus, B. thetaiotaomicron, B. vulgatus, B. plebeius, B. uniformis, B. salyersai, B. pyogenes, B. goldsteinii, B. dorei and B. johnsonii*. The related Parabacteroides genera includes *P. distasonis* and *P. merdae*, and strains thereof. Other species of *Bacteroides* are described, for example, in Clinical Microbiology Reviews, Vol. 20, no. 4, October 2007, p. 593-612 and Approved List of Bacterial Names from NCBI, http://www.bacterio.net/-alintro.html#b and http://www.ncbi.nlm.gov/books/NBK819/.

Suitably a mannan-inducible expression system in accordance with the invention may be used in any *Bacteroides*.

Particularly preferred for the recombinant bacteria expression system and vaccine/pharmaceutical compositions in accordance with the present invention is *Bacteroides thetaiotaomicron* (Bt) (VPI-5482), and strains thereof, including GH193, GH359 and GH364, for example.

Gram-negative bacteria such as *Bacteroides* produce extracellular outer membrane vesicles (OMVs) which may play a role in communicating with host cells in the lower GI-tract, in vivo. Vesiculation and OMV production is a fundamental characteristic of Gram-negative bacteria unrelated to bacterial lysis or membrane instability that fulfils key requirements of a prokaryotic secretion process (McBroom et al., 2007). OMVs may be isolated from *Bacteroides thetaiotaomicron* (Bt.), *B. ovatus, B. xylanisolvens, B. fragilis, B. stercoris* and *B. dorei* (Stentz et al. 2015). OMVs produced by the prominent commensal gut bacterium *Bacteroides thetaiotaomicron* (Bt) contain an inositol polyphosphate phosphatase (BtMinpp) that is structurally similar to mammalian Minpp1 and interacts with cultured intestinal epithelial cells to promote intracellular Ca2+ signalling. OMVs from *B. thetaiotaomicron* parental cells have also been shown to be normally produced in vivo in the GI-tract and associate with and are taken up by the intestinal epithelium.

Advantageously, in one embodiment, OMV's derived from Bt may be associated with a lower incidence of the development of intestinal inflammation when compared to OMVs derived from other bacteria.

Antigen Sequences

Suitable antigen sequences for use in any aspect or embodiment of the invention as described herein include any antigens that may be candidate antigens for use in the treatment of a pathogenic infection such as, for example, a bacterial or viral infection. In one embodiment of any aspect of the invention, an antigen sequence may be any previously validated candidate vaccine antigen. In another embodiment, the antigen sequence may be one derived from *Salmonella*, including those human pathogenic serovars including *Salmonella enterica* serovar *Typhi*. Examples of Salmonella antigens include SseB, OmpD, IroN and shdA. Other suitable *Salmonella* antigens will be known to those skilled in the art and include those described and exemplified herein. Other embodiments include antigen sequences derived from norovirus, such as GII-4, for example. Other norovirus antigens are described herein or will be known to those skilled in the art.

Such suitable antigens may be derived from common human pathogens. In another embodiment, suitable antigens may be derived from common animal pathogens and in particular pathogens that cause infections and/or disease in farm animals.

A Therapeutic Peptide, Polypeptide or Protein

As described herein, the present invention also relates to OMVs containing a therapeutic peptide, polypeptide or protein which are generated from recombinant gut commensal bacteria. Suitable therapeutic peptides, polypeptides or proteins can include, for example, insulin, growth hormone, prolactin, calcitonin, luteinising hormone, parathyroid hormone, somatostatin, thyroid stimulating hormone, vasoactive intestinal polypeptide, trefoil factors, cell and tissue repair factors, transforming growth factor beta, keratinocyte growth factor, a structural group 1 cytokine adopting an antiparallel helical bundle structure such as IL-2, IL-3, IL-4, IL-5, IL-6, IL-7, IL-9, IL-10, IL-11, IL-12, IL-13, GM-CSF, M-CSF, SCF, IFN-γ, EPO, G-CSF, L1F, OSM, CNTF, GH, PRL or IFNalpha/beta, a structural group 2 cytokine which are often cell-surface associated, form symmetric homotrimers and the subunits take up the conformation of beta-jelly roll described for certain viral coat proteins such as the TNF family of cytokines, eg TNFalpha, TNFbeta CD40, CD27 or FAS ligands, the IL-1 family of cytokines, the fibroblast growth factor family, the platelet derived growth factors, transforming growth factor beta and nerve growth factors, a structural group 3 cytokine comprising short chain alpha/beta molecules, which are produced as large transmembrane pre-cursor molecules which each contain at least one EGF domain in the extracellular region, eg the epidermal growth factor family of cytokines, the chemokines characterised by their possession of amino acid sequences grouped around conserved cysteine residues (the C—C or C—X—C chemokine subgroups) or the insulin related cytokines, a structural group 4 cytokine which exhibit mosaic structures such as the heregulins or neuregulins composed of different domains, eg EGF, immunoglobulin-like and kringle domains. Alternatively, the biologically active polypeptide can be a receptor or antagonist for biologically active polypeptides as defined above.

Suitable therapeutic peptides, polypeptides or proteins can be a neurotransmitter, a neuroactive or a neuromodulator, for example tachykinin peptides such as substance P (SP) or neurokinin A (NKA). Other suitable therapeutic peptides, polypeptides or proteins may include those involved in appetite control, such as, for example, ghrelin, PYY, insulin or leptin.

Suitably a therapeutic peptide, polypeptide or protein for use in any aspect or embodiment of the invention may be for the treatment of inflammatory gut disease such as inflammatory bowel disease (IBD) which includes the disorders Crohn's disease and ulcerative colitis.

Suitably a therapeutic peptide, polypeptide or protein for use in any aspect or embodiment of the invention may be expressed in the form of a precursor protein that is further processed post-translationally to produce the active form of the therapeutic peptide, polypeptide or protein.

Suitably, a therapeutic peptide, polypeptide or protein for use in any aspect or embodiment of the invention may be a peptide, polypeptide or protein with direct therapeutic effect, for example a protein hormone.

Suitably a therapeutic peptide, polypeptide or protein for use in any aspect or embodiment of the invention may be a peptide, polypeptide or protein with indirect therapeutic effect, for example an enzyme that catalyses the production of a biologically active product with therapeutic effects. The production of the biologically active product with therapeutic effects may occur inside the cells of the recombinant gram negative commensal gut bacterium, for example if the therapeutic peptide, polypeptide or protein is an enzyme and the substrate of the enzyme is present in or provided to the recombinant gram negative commensal gut bacterium. In this way the OMV produced from the gram negative commensal gut bacterium may contain the therapeutic peptide, polypeptide or protein in addition to the product of the therapeutic peptide, polypeptide or protein; alternatively the production by the therapeutic peptide, polypeptide or protein of a biologically active product with therapeutic effects may occur after the delivery of the OMV to the body.

Other aspects or embodiments are provided in the following numbered clauses:

1. A recombinant gram negative commensal gut bacterium comprising an expression system for expression of an antigen in an outer membrane vesicle (OMV).
2. A recombinant gram negative commensal gut bacterium according to clause 1, wherein the gram negative commensal gut bacterium is from the *Bacteroides* genus.
3. A recombinant gram negative commensal gut bacterium according to clause 1, wherein the gram negative commensal gut bacterium is *Bacteroides thetaiotaomicron* (Bt).
4. A method for preparing an outer membrane vesicle (OMV) for use as a vaccine comprising generating a gram negative commensal gut bacterium that expresses an antigen in its OMV, cultivating the bacteria under conditions for producing OMV and isolating OMV containing an antigen.
5. A method according to clause 4 wherein the gram negative commensal gut bacteria is *Bacteroides thetaiotaomicron* (Bt).
6. A method according to clause 4 or 5 wherein the antigen expression is inducible.
7. An antigen-containing OMV for use as a medicament.
8. An antigen-containing OMV for use as a vaccine.
9. An antigen-containing OMV according to clause 7 or 8 for mucosal administration.
10. A pharmaceutical composition comprising an OMV isolated from a recombinant gram negative bacteria according to any of clauses 1 to 3.
11. A pharmaceutical composition according to clause 10 further comprising a pharmaceutically acceptable excipient.
12. A pharmaceutical composition according to clause 10 or 11 further comprising an adjuvant.
13. An antigen-containing OMV or a pharmaceutical composition according to any of clauses 7 to 12 wherein the OMV are derived from *Bacteroides thetaiotaomicron* (Bt).
14. A recombinant gram negative commensal gut bacteria, a method, an antigen-containing OMV or a pharmaceutical composition as claimed in any preceding claims wherein the antigen is derived from *Salmonella, Campylobacter* or norovirus, such as GII-4.
15. A mannan-controlled gene expression system comprising:
    - a mannan-inducible promoter region of an alpha-1,2-mannosidase gene;
    - a ribosomal binding site;
    - a multiple cloning site; and
    - a transcriptional terminator.
16. A gene expression system according to clause 15 wherein said gene expression system is for use in a recombinant bacteria for the production of antigen-containing OMVs.

Various further aspects and embodiments of the present invention will be apparent to those skilled in the art in view of the present disclosure.

All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

EXAMPLES

Example A—A Mannan-Inducible Expression System

There is considerable interest in studying the function of *Bacteroides* species resident in the human gastrointestinal (GI) tract and the contribution they make to host health. Reverse genetics and protein expression techniques, such as those developed for well-characterised *Escherichia coli* cannot be applied to *Bacteroides* species as they and other members of the Bacteroidetes phylum have unique promoter structures. The availability of useful *Bacteroides*-specific genetic tools is therefore limited. Here the present inventors describe the development of an effective mannan-controlled gene expression system for *Bacteroides thetaiotaomicron* containing the mannan-inducible promoter-region of an α-1, 2-mannosidase gene (BT_3784), a ribosomal binding site designed to modulate expression, a multiple cloning site to facilitate the cloning of genes of interest, and a transcriptional terminator. Using the *Lactobacillus* pepI as a reporter gene, mannan induction resulted in an increase of reporter activity in a time- and concentration-dependent manner with a wide range of activity. The endogenous BtcepA cephalosporinase gene was used to demonstrate the suitability of this novel expression system, enabling the isolation of a His-tagged version of BtCepA. The present inventors have also shown with experiments performed in mice that the system can be induced in vivo in the presence of an exogenous source of mannan. By enabling the controlled expression of endogenous and exogenous genes in *B. thetaiotaomicron* this novel inducer-dependent expression system will aid in defining the physiological role of individual genes and the functional analyses of their products. Such an inducible expression system also has applications to expression systems for producing proteins of interest e.g. antigens, especially in the generation of antigen-containing OMVs in accordance with the invention.

Inducible expression systems are essential molecular tools designed to perform phenotypic examinations of deletion mutants complemented for one or several genes of interest with the aim of defining the role and function of the expressed protein(s). This procedure often requires the use of tuned gene regulation which is particularly critical for the study of genes exhibiting toxic effects when expressed above normal physiological levels.

There is considerable interest in using dominant members of the human intestinal microbiota such as *B. thetaiotaomicron* as a model system to understand and identify the bacterial factors that are important for successful colonization of the GI-tract and the establishment of microbe-host mutualism. *B. thetaiotaomicron* has the capacity to utilize a wide variety of otherwise indigestible dietary plant polysaccharides and host-derived glycans as a source of carbon and energy (Salyers et al., 1977). The functional analysis of *Bacteroides* genes and metabolic pathways is however constrained by a lack of genetic tools. The genetic tools developed for model microorganisms such as *Escherichia coli* are of very limited use for *Bacteroides* species that have promoter structures with a unique consensus sequence (Bayley et al., 2000) recognized by its core RNA polymerase and its own unusual primary sigma factor (Vingadassalom et al., 2005). Parker and Smith circumvented this obstacle by engineering a *B. fragilis* promoter to which an *E. coli* promoter-regulatory region was added to construct an isopropyl b-D-1-thiogalactopyranoside (IPTG)-inducible expression system adapted to *B. fragilis* (Parker and Jeffrey Smith, 2012). However, the range of activity of this engineered *Bacteroides* expression vector is only 7 to 10 fold, which is a limiting factor when larger changes of protein expression are needed. Recently, Mimee et al. (Mimee et al., 2015) developed this system further by investigating the positional effects of operator sites on gene expression. This strategy produced IPTG-inducible promoters eliciting up to 22-fold changes in gene expression. The authors expanded further the range of gene expression (up to 10,000-fold range) using combinations of constitutive *Bacteroides*-derived promoters and ribosome binding sites.

Here the present inventors describe the development of an inducible gene expression system for *B. thetaiotaomicron* that is based upon an endogenous mannan-inducible promoter. This system has proven effective for the controlled expression of the β-lactamase BtCepA resulting in *B. thetaiotaomicron* displaying a broad range of minimum inhibitory concentrations (MIC) of ampicillin in a dose-dependent manner which correlated with mannan-induced BtCepA enzyme levels.

1. Designation of a *B. thetaiotaomicron* Inducible Promoter

In order to develop an inducible gene expression system for use in *B. thetaiotaomicron* publicly available microarray data were examined for inducible genes exhibiting a low basal expression level, and a high expression level (increased by more than 100-fold) in the presence of the inducer. Genes repressed by glucose and induced in the presence of other defined carbon-sources were identified using the NCBI Gene Expression Omnibus web tool (http://www.ncbi.nlm.nih.gov/geo/, series GSE11962) and obtained by transcriptional profiling of *B. thetaiotaomicron* with the aim of establishing the mechanisms underlying host glycan foraging (Martens et al., 2008). Among possible candidates the BT_3784 gene encoding an α-1,2-mannosidase that is part of the polysaccharide utilization locus (PUL) 68 (4) later named MAN-PUL2 (Cuskin et al., 2015) and is induced by the yeast polysaccharide α-mannan, was selected. A 273-base pair DNA fragment located upstream of the BT_3784 gene was cloned in front of the peptidase I reporter gene (Klein et al., 1994) in an expression vector created to express medium levels of protein in *Bacteroides* species (Wegmann et al., 2013) (FIG. 1A). The resulting construct hosted by *B. thetaiotaomicron* created the strain GH193, which was tested for its capacity to conditionally express PepI used as a reporter.

2. Plasmid Constructions

*E. coli* strain JM109 was used for routine cloning and DNA manipulations. Cultures were grown in Luria Bertani (LB) medium at 37° C. Ampicillin (200 μg/ml) was added when appropriate. The *E. coli* strain J53/R751 was supplemented with 200 mg/ml trimethoprim when grown for 18 h. Plasmids constructed in *E. coli* were mobilized into *Bacteroides* strains by triparental mating using J53/R751 as the conjugal helper strain (Shoemaker et al., 1986). Electrocompetent *E. coli* cells were prepared and transformed by the method of Sambrook and Russell (2001). To remove the P1 promoter from pGH022, a 228-bp fragment was amplified from pGH022 (see Table 1 for a list of plasmids) using primer f-noPpepI (see Table 2 for a list of primers), which contained the restriction sites SphI, NcoI, XhoI, and Eco47III and incorporated the transcription initiation site (TIS) and a ribosome binding site for medium level protein expression (RBSmed; original name RBSxyl-20 in Wegmann et al. (2013), and primer r-ppepI/NotI, located 157 bp downstream of the start codon of pepI. This fragment was digested with SphI and NotI, and cloned into SphI- and NotI-digested pGH022 to create pGH063. The 282-bp region located upstream of gene BT_3784 (putative alpha-1,2-mannosidase) was amplified from *B. thetaiotaomicron* VPI-5482 genomic DNA using primers f-3784_3786 and r-3784_3786_sp. This fragment was digested with SphI and cloned into SphI- and Eco47III-digested pGH063 to create pGH066, thereby inserting the BT-3784 promoter (P3784). To replace the region spanning the P1 promoter to the $RBS_{med}$ sequence of pGH022 with the P3784 promoter and a low level protein expression ribosome binding site equivalent ($RBS_{low}$; original name Shine Delgarno 8 (SD8) in Wegmann et al. (2013), splice overlap extension PCR was employed. To this end, Amplicon 1 was generated from pGH066 using primers f-$RBS_{low}$-pepI and primer r-3784_3786_sp. Amplicon 2 was generated from pGH001 using primers r-3784 $RBS_{low}$ and r-ppepI/NotI. Using a mixture of amplicon 1 and 2 as a template and primers r-3784_3786_sp and r-ppepI/NotI, splice PCR was performed. A 452-bp SphI- and NotI-digested fragment of this PCR product was then used to replace the corresponding 329-bp fragment of pGH022 to create pGH105. Insert sequences were amplified from pGH066 using either primer f-$RBS_{med}$ MCS or primer f-$RBS_{low}$ MCS, together with primer r-3784_3786_sp. A 297-bp ($RBS_{med}$) or 292-bp ($RBS_{low}$) SphI- and NcoI-digested fragment of each PCR product was used to replace the corresponding 169-bp fragment of pGH020. This resulted in construction of plasmid pGH106 for medium expression and pGH107 for low expression. The primer pair ccr_amont2 and ccr_aval2 was used to amplify a 1,500 bp region carrying ermF from the plasmid pFD516 (Smith et al., 1995). The ermF fragment was digested with NdeI and cloned into NdeI-digested (blunted) and NsiI-digested pGH106 or pGH107 to replace the existing 1,839-bp fragment of each, to create pGH117 ($RBS_{med}$) and pGH122 ($RBS_{low}$) respectively. Primers Tev-His6_linker 5' and Tev-His6_linker 3' were annealed to form a 66-bp NcoI-StuI-SmaI linker with NcoI and SmaI compatible ends enabling the direct cloning of this fragment into NcoI- and SmaI-digested pGH117, to create $pGH125_{med}$. The presence of this Tev/6×His-tag linker supplies the option to clone a gene of interest into the NcoI and StuI sites of pGH125med, the result of which is the addition of an epitope recognition site for the TEV protease enzyme followed by a 6×His-tag to the C-terminus of the final expressed protein.

3. Effect of Carbon Source on BT_3784 Promoter Activity

All *E. coli* and *B. thetaiotaomicron* strains were grown in either Brain Heart Infusion (BHI) medium (Oxoid/Thermo Fisher, Basingstoke, UK) supplemented with 0.001% hemin (BHIH) or in *Bacteroides* Adapted Defined Medium (BDMA, see Table 3) adapted from Martens et al. (2008). Antibiotics were added as selective agents when appropriate: gentamicin (200 μg/ml), erythromycin and tetracycline (5 μg/ml). Cultures were incubated under anaerobic conditions at 37° C. The reporter activity of strain GH193 was tested after growth in rich medium (BHIH) and in minimal medium (BDMA) supplemented with different carbon-sources, in the presence or absence of the exogenous mannan (FIG. 1B). In minimal media the growth rate of strain GH193 was similar in all cases independent of the carbon source present with the exception of mannan for which GH193 exhibited slower growth with a generation time of 130 minutes compared to 90 minutes under the other conditions. In rich media, reporter activity in GH193 did not significantly increase upon mannan induction. As BHI (to which hemin (H) was added) contains 0.2% glucose, this suggests that glucose represses the expression of BT_3784 as reported by Martens et al. (2008), despite the presence of mannan. However, in minimal medium supplemented with glucose as the major carbon source mannan induction resulted in an increase of PepI activity of about 15-fold (FIG. 1B) indicating that additional sources of repression are most likely present in BHI mixture. For the PepI assay, cultures (200 ml) were grown in duplicate to an optical density at 600 nm of 0.5 before induction. To determine the optimal inducer concentration, mannan was added to 20 ml aliquots at a final concentration of 0, 0.1, 1.0, 5.0, 10, 50 or 100 mg/L. Following a 2-h induction period cells were collected by centrifugation at 6,000 g for 15 min at 4° C. The preparation of *B. thetaiotaomicron* cell-free extracts was performed as previously described (Wegmann et al., 2013). To determine the optimal induction time, mannan was added to a final concentration of 100 mg/l and incubation continued. Subsequently, 20 ml samples were collected over time and the cells harvested as described above. The protein concentration and peptidase I activity was determined according to the method described by Wegmann et al. (2013). Specific activity is expressed as nanomoles of p-nitrophenol released from the chromogenic substrate per milligram protein per minute. Mannan-induced PepI activity for cells grown on galactose, lactose and xylose was increased 110 to 120-fold compared to the respective control cultures lacking mannan (FIG. 1B). The PepI activities measured for cells grown on arabinose and mannose in the presence of mannan, although lower, were still 87 and 109 times higher, respectively, than control cultures lacking mannan (FIG. 1B). Not surprisingly, despite a slower growth rate, cells grown on mannan exhibited high PepI activity. Among the carbon sources tested in this study, only glucose negatively affected mannan induction of the BT_3784 promoter (P3784). Glucose negatively regulates expression of α 1,2 mannosidase as previously observed in other *Bacteroides* species for the expression of other glycosidases such as β-glucosidase in *B. ruminicola* (Strobel and Russell, 1987) or xylanase in *B. ovatus* (Hamady et al., 2008). Of note, low levels of PepI activity were detectable in the absence of mannan consistent with previous data showing low level of *B. thetaiotaomicron* PUL expression in conditions lacking the relevant substrates (Sonnenburg et al., 2006, Martens et al., 2009 and Sonnenburg et., 2006). Of significance, the monosaccharide mannose, one of the major end-products of mannan enzymatic hydrolysis (Düsterhöft et al., 1993), does not affect expression of the α 1,2 mannosidase gene although this substrate has been shown to have an inhibitory effect on the utilization of several hexoses including glucose and pentoses in *B. thetaiotaomicron* (Degnan and Macfarlane, 1995).

4. Effect of Mannan Concentration and Induction Time on Promoter Activity

The pepI gene of *Lactobacillus delbrueckii* subsp. *lactis* encoding peptidase I and the BtcepA gene encoding a *B. thetaiotaomicron* β-lactamase were used as reporters to study promoter activity in *B. thetaiotaomicron* in response to the mannan inducing agent. The *B. thetaiotaomicron* strains under study were grown in BDMA. The response of P3784 to increasing concentrations of mannan was tested for cells grown in minimal medium containing xylose. The strains tested were GH193, containing a *Bacteroides* expression vector that contains a translation initiation signal designed for medium expression (Wegmann et al., 2013) and GH287, containing a vector designed for low expression (Wegmann et al., 2013) to ensure that the widest range of expression levels were covered with the lowest basal activity. The basal level activity of P3784 measured for GH287 was 5-fold lower than for strain GH193 (FIG. 2A). For both strains GH193 and GH287, PepI activity reached its peak at mannan concentrations as low as 50 mg/L (FIG. 2A) which corresponds to 0.005% of mannan. To further optimize the conditions of induction, the minimum induction time required to generate the highest level of reporter activity was determined. The response of the promoter was assessed over a time-course of mannan-induction in strain GH193 incubated with 50 mg/L mannan. PepI activity was detectable after 30 min and continued to increase thereafter with the maximal activity reached after 90 min (FIG. 2B). In the case of GH287, the strain containing the low-RBS-$P_{3784}$ construct, maximal activity was also reached after 90 min. To facilitate the controlled expression of genes of interest in *Bacteroides*, plasmids were constructed that contain a multiple cloning site in the position of the pepI reporter, resulting in construction of plasmid pGH106 for medium expression and pGH107 for low expression, as detailed above.

5. Mannan-Controlled Resistance to Ampicillin

Since optimization of this novel gene expression system was based upon the use of a heterologous reporter gene, the system was validated by determining if it can be used to study *B. thetaiotaomicron* genes. For this purpose, the complementation of a deletion mutant of BtcepA (Stentz et al., 2015), a cephalosporinase gene involved in the resistance of bacterial cells to β-lactam antibiotics, was undertaken. The primer pair Lactamase_F and Lactamase EcoRI_R was used to amplify an 885-bp region from *B. thetaiotaomicron* VPI-5482 genomic DNA encoding BtcepA. The BtcepA fragment was digested with EcoRI and cloned into the NcoI-digested (blunted) and EcoRI-digested pGH122 ($RBS_{low}$) or pGH117 ($RBS_{med}$) to create plasmids pGH141 and pGH142 respectively, which were used to transform the *B. thetaiotaomicron* ΔβBtcepA strain GH221. The β-lactamase activity was measured after 2 h of induction with increasing concentrations of mannan (Table 4). For the β-lactamase assay, cultures (200 ml) were grown in duplicate to an optical density at 600 nm of 0.5 before inducing 20 ml aliquots with varying levels of mannan (see Table 4) or 5 mg/L of cefotaxime. Periplasmic proteins were prepared as described by Stentz et al. (Stentz et al., 2015). β-lactamase activity was assessed spectrophotometrically by hydrolysis of nitrocefin according to the manufacturer's instructions (Calbiochem). The means and standard deviations presented are based upon two biological replicates with three technical replicates each. Use of increasing concentrations of mannan with the low-expression system gradually restored up to two-thirds of β-lactamase activity produced in the wild-type strain. With the medium expression system graduated and increasing levels of β-lactamase activity were produced which eventually exceeded the native expression levels of BtCepA. The use of the low and medium variants permitted a range of induction from 1 to 1155 fold activity values. The basal level measured for the low expression system was negligible since it represented only 2.7% of the activity measured for the wild-type control strain. To establish how these measured activities translate into resistance to β-lactam antibiotics the minimum inhibitory concentration (MIC) of the β-lactam antibiotic ampicillin was determined for each variant strain grown in the presence or absence of mannan. The measured MIC values closely correlated with β-lactam activities measured in the corresponding strains (FIG. 10) with values ranging from 4 mg/L to 2048 mg/L.

6. Production and Purification of Recombinant BtCepA

Protein fusion tags are essential tools designed to improve recombinant protein expression yields, facilitate protein purification and accelerate the determination of protein structure, function and interactions. Our system was utilized for the expression of the recombinant His-tagged BtCepA protein. To this end, the C-terminus of the BtcepA coding region was fused to the hexahistidine affinity tag encoded on pGH125med. The strain GH402 containing the construct was induced for 5 h in the presence of mannan and the cell periplasmic fraction was obtained. Recombinant BtCepA containing a C-terminal His-tag was purified by affinity chromatography and loaded on a SDS-PAGE (FIG. 3). BtCepA[His]6 from *B. thetaiotaomicron*, cultures (100 ml) were grown to an optical density at 600 nm of 0.5 before inducing for 2-h with 100 mg/ml of mannan. Cells were collected in two aliquots of 50 ml by centrifugation at 3,500 g for 10 min at ambient temperature. Each 50 ml cell pellet was processed to extract its periplasmic proteins as described by Stentz et al. (2015) with the exception that a final volume of 0.4 ml of ice-cold MgSO4 5 mM solution was used. To the recovered osmotic shock fluid, 63 ml of 10× concentrated lysis buffer ($NaH_2PO4$ 0.5 M, NaCl 0.3 M, imidazole 0.1 M, pH8) was added before the final volume was adjusted to 600 ml using 5 mM MgSO4. Contaminating cell debris was removed by centrifuging at 12,000 g for 15 mins at 4° C. before continuing the purification process using a Ni-NTA spin Kit (Qiagen, UK). Purification of BtCepA[His]6 was performed under native conditions according to the manufacturer's instructions. As a control, native BtCepA was expressed under the same conditions with a SDS-PAGE-resolved band corresponding to the protein detected in periplasmic extracts (FIG. 3). A band of a slightly higher molecular weight was detected for the BtCepA-$His_6$ fusion protein attributable to the protein tag. After purifying and concentrating the eluted band, a single species corresponding to BtCepA-His6 was obtained whereas no comparable band was detected for the empty vector control with no protein corresponding to BtCepA-His6 detected in the flow-through (FIG. 3). Selected spots were picked on the single band obtained after SDS-PAGE and trypsin-digested using the ProPick Spot Picker (Genomic Solutions) and ProGest protein digestion robot (Genomic Solutions) prior to peptide mass fingerprinting on an Ultraflex II MALDI173 TOF-TOF (Bruker) using an offline version of Mascot (Matrix Sciences) searching against *B. thetaiotaomicron* sequences. Using peptide mass fingerprinting, the band was identified as BtCepA. An efficient system was developed that allows the purification of *B. thetaiotaomicron* recombinant proteins produced in their native host, and in this context, recombinant proteins are more likely to retain their native characteristics.

7. Mannan-Induced BtCepA Expression in the Mouse Gut

"α-mannan is a fungal cell wall glycan that contains α-mannosidic linkages similar to those found in the core regions of N-linked glycans present on secreted mucus and epithelial surfaces" (Martens et al., 2011). However, expression levels of the PUL genes involved in mannan utilization in mice fed a diet lacking exogenous α-mannan were only partial when compared to other PULs showing high activity in vivo (Martens et al., 2008). The effectiveness of the mannan induced system was tested in vivo in seven-week-old male C57BL/6J WT mice with established *B. thetaiotaomicron* within the intestine, housed in a conventional animal facility after treating for 3 days with 1 mg/ml ampicillin and 1 mg/ml neomycin administered via drinking water. To achieve this, the strain GH361 containing the BtCepA gene controlled by the inducible low expression system (Table 1) was administered by oral gavage (1×108 colony-forming units (CFU) in 100 μl of phosphate buffered saline) to two groups of 4 mice. One of the groups (Group A) were given drinking water with containing 2.5% (v/v) mannan-oligosaccharide supplement (ActiveMOS, Orffa, Werkendam, The Netherlands) prepared treating the powder (10% w/v) with 1% NaOH at 100° C. for 1 h, cooling and neutralizing to pH7 with dilute HCl solution (Huang et al., 2010). After 2 days both groups of mice were similarly colonized with GH361 as seen by counting the CFU in fecal samples (FIG. 4) indicating that exposure to mannan did not impact on the ability of *B. thetaiotaomicron* to colonize the mouse intestine. Both groups of mice were challenged every other day via i.p. injection with ceftriaxone (0.4 mg/mice), a thirdgeneration cephalosporin that is excreted via the biliary route and affects the colonic microbiota (Arvidsson et al., 1982). The MICs of ceftriaxone determined for GH361 were 8 mg/L when cells were grown in the absence of mannan and 64 mg/L when mannan was added to the growth medium. Three successive doses of ceftriaxone had no effect on the levels of GH361 in group A that had been given mannan; however, the levels of GH361 that had not been given mannan (group B) decreased approximately 15-fold (FIG. 4). Increasing further the amount of ceftriaxone to 0.8 mg showed that both groups were equally affected and population levels decreased significantly. The moderate impact of mannan observed on GH361 resistance to ceftriaxone is most likely due to the induction of promoter activity by endogenous mannan and/or derivatives. The differences obtained in GH361 colonization between the groups with and without added mannan ($p<0.01$) suggests this system could be of use in in vivo studies. For example, it is conceivable to consider replacing the mannan promoter with PUL promoters regulated by plant-derived inducing agents such as arabinogalactan whose effectiveness was recently demonstrated (Mimee et al., 2015). Animal experiments were conducted in full accordance with the Animal Scientific Procedures Act 1986 under Home Office approval.

Conclusion

A novel mannan-inducible gene expression system for use in *B. thetaiotaomicron* has been generated. We have shown that the gene BT_3784 is regulated in response to mannan and have combined the region located upstream of gene BT_3784 with two distinct ribosomal binding sites that allow the amount of gene expression to be tightly regulated. This mannan-controlled gene expression system is tunable via altering of the mannan concentrations and, in combination with ribosomal binding sites RBSmed and RBSlow (Wegmann et al., 2013), generates more than a 1000-fold range of promoter activity. The system is remarkably efficient as it only requires concentration of mannan as low as 50 mg/l to be fully induced. The vectors described in this study constitute together a valuable tool for expressing *Bacteroides* genes and purifying their products, as well as studying *Bacteroides* cell physiology. The ability to tune or regulate the expression level is advantageous because it allows different amounts of heterologous peptides or proteins to be secreted, which is of value in cases where excess production and/or high levels of the protein may have adverse biological effects.

Example B—Generating OMVs

Bt strains capable of expressing and packaging candidate bacterial and viral vaccine antigens into their OMVs are engineered. The size of Bt OMVs varies (<50-300 nm) which may influence their cargo and vaccine antigen content, and how they interact with host immune cells. Engineered Bt OMV vaccine antigen formulations are characterised using proteomics and mass spectroscopy of size fractionated OMVs. This information is important in both identifying pathways of uptake in the gut, the targeting of inductive mucosal immune sites, and interactions with and acquisition by mucosal immune cells and in particular, antigen presenting cells (APCs).

The capability of Bt OMV vaccines to interact with APCs and generate local and systemic host immune responses is determined. In vitro and in vivo model systems are used to investigate mechanisms and outcomes of OMV-immune cell interactions after oral or intranasal administration. Established transcytosis models are used to demonstrate that microfold (M) cells play an important role in the initial uptake of OMVs, which they subsequently deliver to dendritic cells and macrophages in their basolateral pockets. Two unique transgenic mouse lines expressing fluorescent reporter proteins in their APCs, Csf1r-EGFP (MacGreen) and csflr-gal4VP16/UAS-ECFP (MacBlue), are used in conjunction with intravital 2-photon and confocal microscopy to demonstrate that OMV exposure stimulates direct sampling by APCs in the lamina propria and their subsequent migration and dissemination of OMVs to peripheral lymphoid tissues.

Demonstration that Bt OMV Vaccines can Induce Specific Immunity and Protection.

Vaccination of mice with OMV vaccine formulations is used to demonstrate the ability of OMV vaccines to elicit antigen-specific mucosal and systemic antibody (IgA/IgG) and CD4 T cell responses. These immune parameters are surrogates or determinants of protective immunity as determined by challenging vaccinated animals with live virulent pathogens and assessing pathogen containment and dissemination from the gut to peripheral tissues.

Strains of Bt are developed that stably express previously validated candidate vaccines antigens of *Salmonella* (SseB, OmpD and shdA) and norovirus (GII-4 capsid proteins) in OMVs, the physical and chemical characteristics of which are fully defined for optimal oral or intranasal administration. The pathways of OMV uptake and their ability to target microfold (M) cells in the intestinal and nasal mucosa and associated antigen presenting cells (APCs) are demonstrated by imaging and tracking OMVs in vivo. A successful OMV vaccine may be one which can generate antigen-specific CD4 T cells and IgA antibodies both locally and systemically that are capable of protecting against infectious challenge.

Rationalised design and selection of secretion signal sequences for efficient targeting of vaccine antigens to OMVs is carried out. Bt-generated OMV vaccine formulations and how their size influences vaccine antigen content and distribution in OMVs are characterised. Pathways of OMV uptake in vivo and their requirements for accessing M cells and mucosal APCs are established. The generation of specific immunity and protection against infection by OMV vaccines is defined. This provides the rationale for testing Bt OMV vaccines in animals and humans. The logical disease and target populations are *salmonellosis* in farm animals (pigs and chickens) and norovirus infection in vulnerable and at risk human populations Demonstration of Feasibility of Vaccine Ag Selections: *Salmonella*

The species *Salmonella enterica* comprises distinct serovars that infect a broad range of hosts with *Typhimurium* and *Enteritidis* being significant pathogens of livestock and humans and *Typhi*, an exclusive human pathogen that causes typhoid fever. *S. typhimurium* infection of domestic livestock and fowl worldwide results in a spectrum of outcomes ranging from severe disease to asymptomatic carriage, which via contamination of the food supply is a major source and route of infection in humans. Reducing the risk of food-borne infection is an important driver in developing more effective vaccines for farmed animals particularly in considering the banned prophylactic use of antibiotics (in Europe) and increasing multi-drug resistance. Currently available vaccines provide only moderate levels and limited duration of protection and incomplete coverage of clinically relevant serovars (Bumann, 2014). Protective *Salmonella* Ag have been identified as being surface-exposed or secreted (Bumann, 2014) numbering more than 200.

Approximately 50 of these are expressed during infection in the mouse typhoid model with nine conferring some degree of protective immunity in mice (FliC, SseB, OmpD, CirA, IroN, T0937, SlyB, PagN, and Ssel) (Bumann, 2014, Rollenhagen et al., 2004, Gil-Cruz et al., 2009, Lee et al., 2012 and Reynolds et al., 2014). The SPI-2 translocon subunit SseB is a particularly promising vaccine Ag, capable of generating (Ab) and T cell responses in both mice and humans (Lee et al., 2012). Identifying Ag required for the persistence and shedding of *Salmonella* in the intestine has revealed additional candidate vaccine Ag including the shdA gene that is required for persistence in the mouse caecum (Kingsley et al., 2002). With the specific aim of demonstrating the ability of Bt-derived OMVs to deliver, rather than authenticate, candidate vaccine Ag to mucosal sites the choice of Ag for OMV delivery is rationalized to those with the potential to limit colonization (ShdA) and infection of the host by eliciting protective host immune responses (OmpD and SseB). Our data demonstrates the feasibility of deriving Bt strains expressing *Salmonella* Ag (OmpA) in their OMVs that can elicit specific Ab responses in mice after oral administration (FIG. 5). Bt was engineered to express vaccine antigens. Expression of *Salmonella* OmpA (StompA) in Bt-OMVs was detected by the use of Immunoblotting (IB) of OMV lysates (FIG. 5, A, arrow). Ultrathin sections of Bt StompA+ OMVs were stained with rabbit anti-StompA and anti-rabbit Ig-gold particles and imaged by EM to demonstrate expression of StompA (FIG. 5, A, inset). Levels of anti-StompA IgG in sera of mice (n=6ea.) 28 days post oral gavage with StompA+Bt OMVs (squares) or wildtype Bt OMVs (-triangles) or, after i.p. injection of StompA+Bt OMVs (diamonds) determined by solid-phase ELISA. *p<0.05 comparing IgG levels pre-versus post oral and i.p. StompA+ OMV immunization (FIG. 5, B). Expression of norovirus GII-4 capsid mRNA in recombinant Bt (norov) was detected by RT-PCR. The gyrA gene was used as a control (FIG. 5, C).

Demonstration of Feasibility of Vaccine Ag Selections: Norovirus

Human noroviruses are the leading cause of epidemic gastroenteritis and of foodborne disease outbreaks in Europe (Verhoef et al., 2010). An estimated annual 300 million cases of norovirus infection contribute to roughly 260,000 deaths worldwide, mostly among the very young and elderly (Trivedi et al., 2013). Genogroup II-genotype 4 (GII-4) noroviruses is the predominant genotype circulating in the US, Europe and Oceania over the past decade causing up to 80% of all norovirus outbreaks (Desai et al., 2012). The inability to maintain human noroviruses in cell culture and generate live/killed-attenuated strains has led to the use of monovalent and multivalent vaccines incorporating virus like particles (JT) from different genotypes, including GII-4, that also contain adjuvants. When delivered via (intramuscular) injection these vaccines can generate blocking Ab responses in human volunteers (Lindesmith et al., 2015 and El-Kamary et al., 2010). However, their ability to protect against virus infection has yet to be trialled, or they have missed their primary endpoint in early-phase trials (Bernstein et al., 2015). To date, orally-delivered recombinant norovirus VLPs without adjuvants are immunogenic and capable of eliciting both mucosal and systemic Ab responses in mice and healthy human volunteers (Ball et al., 1999 and Tacket et al., 2003). Mucosal administration of VLPs is an effective route for the delivery of norovirus vaccines. The present inventors have engineered strains of Bt to express genes encoding GII-4 norovirus capsid (FIG. 5) the products of which are expressed in OMVs that are tested for their ability to elicit mucosal and systemic immune responses in vivo after oral delivery and immunisation. The globally dominant VIII-4 strains are a rapidly evolving genocluster with the emergence of antigenically novel strains linked to a period of epidemic gastroenteritis. As such emergence events tend to occur worldwide over a one-year period any candidate vaccine will need to be easily adapted/re-engineered to accommodate antigenic changes in circulating virus strains. The present invention of *Bacteroides* OMV technology is sufficiently adaptable to meet this need.

Engineering Bt to Express Pathogen Ag

The fusion of the N-terminal signal peptide of Bt OmpA to *Salmonella* OmpA facilitates its secretion into Bt OMVs (FIG. 5) with this strategy being repeated for *Salmonella* OmpD and ShdA, and GII-4 norovirus capsid proteins. Functional domains are prioritized for expression if full-length proteins cannot be or are poorly expressed. For example, the Hep-2 (Kingsley et al., 2004a) and A3 (Kingsley et al., 2004b)) regions of ShdA required for fibronectin binding. The recombinant genes are cloned into Bt vectors containing various RBS constructs that provide different expression levels (Wegmann et al., 2013). Secretion of the vaccine Ag into Bt OMVs is assessed by immunoblotting (IB) and/or ELISA with self-assembly of capsid proteins into virus-like particles visualised by EM. Proteins/enzymes that might enhance pathogen virulence such as antibiotic resistance genes identified from the genome sequence and/or OMV proteome are "engineered out" of Bt as has been achieved in eliminating expression of a cephalosporinase (CepA) that is expressed in association with the outer membrane of OMVs (Stentz et al., 2015).

Alternative Approaches to Ag Expression

The technology to generate recombinant Bt strains is well established by the present inventors and has been successfully applied to expressing *Salmonella* and norovirus Ag in Bt and their OMVs (FIG. 5). Alternative approaches in order to express vaccine Ag in Bt OMVs are possible, for example, using different (mix and match) secretion signal sequences identified from the OMV proteome and corresponding Bt genome, or software programs (e.g. SignalP) that predict N-terminal signal sequences of proteins, or by focusing on those Ag that can be expressed that meet the criteria for selection.

Bt OMV Preparation

As demonstrated by the inventors previously (Stentz et al., 2015 and Stentz et al., 2014), OMVs are prepared by a series of filtration and ultracentrifugations of early stationary growth phase cultures of wild type Bt (VPI-5482) and engineered strains expressing *Salmonella* and norovirus Ag. OMV concentration and size distribution are determined by nanoparticle tracking analysis (NTA) using the NanoSight NS500 (Malvern Inst. Ltd) calibrated with silica microspheres (Gardiner et al., 2013). NTA has been successfully used to characterise microvesicles in cultures of human cells and in body fluids (Soo et al., 2012) and provides a fast, direct and reproducible method for determining OMV concentration and size distribution. For comparative purposes conventional OMV determinations based on the ratio of protein content and numbers of viable bacteria are used. EM is used to assess OMV purity and integrity. The internal/external localisation and resistance of vaccine Ag to extracellular proteases is established in a protease-protection assay, incubating OMV preparations with proteases (or mouse caecal contents) prior to D3 analysis (Stentz et al., 2015). The size of Bt OMVs varies (~75-300 nm; FIG. 5) which may influence their vaccine Ag content, and/or their interaction with and uptake by host immune cells. The optimal growth conditions to maximize OMV production with respect to their size and vaccine Ag content are empirically determined. Vaccine Ag expression is confirmed by D3 and/or ELISA of OMV lysates. If the level of OMV production is insufficiently remedied by refining growth conditions hypervesiculating strains of Bt are derived by, for example, mutating genes homologous to *E. coli* and *Salmonella* Deg serine proteases (BT_1312 E values 2e-63 and 4e-76 for DegS and DegP, respectively), which in *E. coli* increases OMV production 100-fold (McBroom et al., 2006). The large-scale bioreactors (15-100 litres) are used for scaling up Bt cultures and OMV production.

Imaging of OMVs

The envelope of isolated OMVs is readily labelled with fluorescent dyes (e.g. FITC, DiI, DiO, PKH26) using standard protocols (Hickey et al., 2015). The content of the OMVs is labelled using fluorescent vancomycin to tag complex peptidoglycan. Data shows that DiI-labelling is suitable for imaging of Bt OMV interactions with intestinal epithelial cells in vivo (FIG. 6). DiL-labelled OMVs (red) were injected into murine ileal loops and 30 min later tissues were snap frozen, sectioned (4 μm), counterstained with DAPI (blue) and imaged by uv microscopy (Zeiss Axiovert). The merged low (top) and high power (bottom) images show co-localisation (bright areas) of OMVs along the crypt villous axis and villus tips. OMVs that may be located within the lamina propria were identified (arrow, FIG. 6).

Bt OMV Proteome Definition

Defining the proteome of Bt OMVs establishes optimal growth conditions in order to maximize vaccine Ag content. It also establishes the distribution of MAMPs (e.g. TLR and NOD ligands) and lyco/lipoproteins that facilitate and enhance host cell interactions (adhesins, mucus-sulphatases), addresses biosafety concerns, and excludes expression of proteins detrimental to host cell function (e.g. toxins, lysins, Ig proteases). The contents of highly purified, density gradient ultracentrifugation (Optiprep)-fractionated (3-4 fractions) OMVs are characterised by proteomics and mass spectrometry in addition to vaccine Ag content (Berlanda Scorza et al., 2008 and Lee, 2007).

Demonstration of the Transcytosis of OMVs Across the Gut Epithelium by M Cells

To mount an immune response, luminal Ag must first be transported across mucosal (e.g. intestinal and nasal) epithelium into the GALT/NALT, which in the GI-tract comprises chiefly the appendix, Peyer's patches (PP), colonic patches and isolated lymphoid follicles. Overlying the GALT/NALT are unique epithelial cells called M cells specializing in the transcytosis of luminal particulate Ag and pathogens (Mabbott et al., 2013). M cell-mediated Ag transcytosis across the follicle-associated epithelium (FAE) of PP is required for the induction of efficient mucosal immune responses (Hase et al., 2009 and Kanaya et al., 2012). The targeted delivery of vaccine Ag to M cells is an effective means of inducing Ag-specific immune responses (Ulmer et al., 2006). M cells are closely associated with mononuclear phagocytes (MNPs) comprising macrophages and classical DCs (Bradford et al., 2011) which sample transcytosed Ag within the M cell's basolateral pocket (Wang et al., 2011). Intestinal epithelial cells and macrophages can acquire Bt-generated OMVs in the intact mouse colon although this has only been shown to date to occur in mice with immunoregulatory deficiencies and defective barrier function (Kang et al., 2013). The normal conditions under which Bt OMV uptake occurs in the GI-tract and nasal cavity are determined.

Established in vivo Ag transcytosis assays (Donaldson et al., 2012) are used to demonstrate the importance of M cells in the initial transcytosis of OMV from the gut lumen and nasal cavity across the FAE to underlying MNP (Knoop et al., 2009, Hase et al., 2009, and Nakato et al., 2012). Groups of C57BL/6 mice (n=4) are gavaged with fluorescent recombinant OMV and fluorescent 200 nm latex beads (as a control tracer) with removal of the entire small and large intestine at intervals afterwards (1-24 h) and bead uptake into the GALT quantified by high-resolution intravital 2-photon microscopy and whole mount immunofluorescent confocal microscopy (FIG. 7) (Donaldson et al., 2015). A range of OMV doses are used guided by prior studies that have orally delivered pathogen-derived OMVs to mice to elicit host immune responses (Collins et al., 2011). OMV and beads are also administered intra-nasally to compare their uptake by M cells in the NALT (Mutoh et al., 2015). By using entire intestines, as well as a range of doses of OMV and exposure intervals the anatomical sites of OMV uptake are demonstrated, along with the optimal dose of OMV and a comparison is made of the kinetics of their uptake. The TNF superfamily member receptor activator of NF-κB ligand (RANKL) has been shown to be the critical factor controlling the differentiation of RANK-expressing enterocytes into M cells (Knoop et al., 2009). Furthermore, M cells are depleted following RANK-signalling blockade by treatment with anti-RANKL Ab. To confirm involvement of M cells in OMV uptake across the gut epithelium, OMV (or beads) are administered to villin-cre+RANKfl/fl mice, where RANKL-dependent M cell differentiation and uptake of particulate Ag is blocked throughout the gut epithelium (Powell et al., 2015). Treatment with recRANKL stimulates the expansion of M cells enhancing uptake of Ag and enteric bacteria (Knoop et al., 2009, Kanaya et al., 2012 and Kimura et al., 2015). It is determined if increasing M cell density enhances OMV uptake from the gut lumen. Groups of C57BL/6 mice are injected i.p. with recRANKL (or PBS as a control) to stimulate M cell development (Knoop et al., 2009 and Kanaya et al., 2012) with M cells numbers within the intestine determined at daily intervals by staining whole mounts of intestine with glycoprotein 2 (Gp2)-specific Ab (Donaldson et al., 2012 and Kobayashi et al., 2013) and comparing numbers of Gp2+ M cells within GALT and the lamina propria. To demonstrate the influence of M cell density on OMV uptake, at the peak of recRANKL-induced M cell induction, mice are gavaged with fluorescent OMV (and fluorescent beads as a control) and the number of OMVs taken up into the lamina propria is determined microscopically (Donaldson et al., 2015, Donaldson et al., 2012 and Kobayashi et al., 2013).

Alternative Approaches to M Cell Uptake

It is also possible in the present invention to incorporate an M cell targeting strategy into OMV vaccine design by incorporating known M cell-binding ligands such as the FimH protein of *Salmonella*, the invasin or OmpH of *Y. enterocolitica* and peptides selected from (phage display) libraries chosen for M cell binding (e.g. Col) that increase local and serum IgA responses (Chionh et al., 2010, Foxwell et al., 2007 and Shima et al., 2014).

Demonstration of OMV Access to and Impact on Intestinal APCs

The interaction of M cell-associated MNP with OMVs and their effect on MNP function is demonstrated. Two unique transgenic mouse lines are used: Csf1r-EGFP+ (MacGreen) mice (Sasmono et al., 2007) in which all the CSF1R+ MNP throughout the GI-tract (macrophages and DC; (Bradford et al., 2011) express high levels of GFP, and Csf1r-gal4VP16UAS-ECFP (MacBlue) mice in which ECFP expression in the GI-tract is limited to DC in the sub-epithelial domes beneath the FAE of the GALT (Sauter et al., 2014) (FIG. 7). These two mouse lines allow the specific uptake of OMVs by distinct MNP populations in the gut in vivo to be studied by immunofluorescent microscopy. Fluorescent recombinant OMVs are administered (as above) by oral gavage (Donaldson et al., 2015) or via injection into the lumen of exteriorized intestinal loops of mice (Donaldson et al., 2012 and Kobayashi et al., 2013). Tissues are imaged by high-resolution intravital 2-photon and confocal microscopy to demonstrate OMV exposure stimulating the direct sampling by MNP in the lamina propria. In the steady state intestinal DC continuously migrate through the lymphatics to the mesenteric lymph nodes (MLN) where they help elicit immunity or tolerance (Cerovic et al., 2013). MacBlue macrophage reporter mice are used to compare the presence of fluorescent OMV within the resident and migratory DC subsets in the gut, MLN and spleen (Sauter et al., 2014, Cerovic et al., 2013 and Houston et al., 2015). The present inventors also demonstrate the ability of Bt OMV vaccines to elicit mononuclear cell recruitment to primary sites of immune induction such as the PP. MacBlue mice are well suited for this as under normal homeostatic conditions they identify scarce populations of monocyte/macrophages and DC in the intestinal lamina propria (5-6% of CD45+ cells; FIG. 7) and MLN, with the number of ECFP+ cells increasing massively in PP in response to mobilising stimuli and cytokines (Sauter et al., 2014). Intestinal DCs can be divided into functionally distinct groups based on CD103 and CD11b (Cerovic et al., 2013). Whereas CD103+ DC are generally considered to be tolerogenic and induce the differentiation of Tregs in the MLN, CD103− DC appear to be more immunogenic and induce the differentiation of INF-γ and IL-17 producing T cells. Ex vivo analysis of cells extracted from intact tissues using multiparameter flow cytometry is also conducted, to identify, phenotype and quantitate the infiltrating MNP. ELISA is used to compare cytokine responses.

Example C—Determining if Bt OMV Vaccines can Induce Specific Immunity and Protection

OMV Recognition by Lymphocytes

*Salmonella* and norovirus infection induce Ag-specific B and T cell responses with protective immunity requiring both humoral and cell-mediated responses (Bumann, 2014). It is therefore important that the chosen *Salmonella* and norovirus vaccine Ag that generate Ag specific adaptive immune responses during natural or experimental infection can, when delivered via OMVs, elicit comparable Ab and CD4 T cell responses. Adult single sex C57BL/6 mice (n=10/grp) are gavaged with three doses of OMV vaccines administered 4 weeks apart. Control groups of animals receive wildtype OMVs, vehicle (PBS) alone or OMVs delivered i.p. Serum samples collected before and 2 weeks after initial immunisation and 2 weeks after the first and second booster immunisations are analysed for total Ig (IgM, IgG and IgG isotypes, and IgA) by sandwich ELISA and for vaccine Ag specific Ig by solid-phase ELISA. Faecal water and the contents of the caecum and small and large intestine harvested at the end point (2 weeks post final booster immunisation) are similarly examined for vaccine Ag specific (IgA) Ab. IFNγ-producing CD4+ T cells play an essential role in controlling virulent *Salmonella* infection in mice (Nauciel, 2000) and in immune clearance in avian *salmonellosis* (Withanage et al., 2005). Evidence for CD4 T activation in OMV vaccinated mice is demonstrated using flow cytometry, identifying changes in expression of surface Ag associated with activation (e.g. CD69, CD80/86, CD44, CD62L, FoxP3; CD44hiCD62Llo) or prior Ag exposure (e.g. KLRG1; (Voehringer et al., 2002), and cytokine production (IFNγ, TNFα, IL-6, IL-12, IL-17, IL-10) amongst splenocytes and intestinal lamina propria cells after re-exposure in vitro to vaccine Ag containing OMVs, using OMVs from wild type Bt, LPS or, anti-CD3 antibodies as control stimuli (Alaniz et al., 2007).

OMV Priming of Pathogen-Specific Protective Immunity

The features of human *salmonellosis* reproduced in the murine model are the natural (oral) route of entry, tissue and cellular tropism of the bacterium, and activation of innate and adaptive immunity (Mastroeni et al., 2004). Mice are challenged i.p. to demonstrate immunity to systemic infection, and by oral challenge to demonstrate that mucosal immunization can contain and prevent dissemination of *S. Typhimurium* from the intestine. C57BL/6 susceptible mice (n=10/grp) are inoculated orally (5×108 cfu) or i.p. (5×103 cfu) with a chloramphenicol resistant variant of *S. Typhimurium* SL1344 and 5 days later mice are culled and cfu in the cecum, mesenteric lymph nodes, liver and spleen are enumerated in homogenised tissue by serial dilution. Selection for chloramphenicol resistance distinguishes the challenge strain from the commensal bacteria in caecal contents. Also, naive or immunized C57BL/6 mice are challenged i.p. (5×103 cfu) with *S. Typhimurium* SL1344 and timed to a predefined endpoint (>15% decrease in body weight) to ethically approximate kill curves. OMV (vaccine Ag+ or Ag−) or mock (PBS) immunized 129svJ resistant mice (n=10/grp) are inoculated with $1\times10^9$ cfu of a chloramphenicol resistant variant of *S. typhimurium* SL1344 and the cfu in fecal pellets determined on days 1, 7, 14 and 21-post inoculation in order to demonstrate the impact of mucosal immunisation on long-term intestinal persistence. Immune cell parameters in infected mice are determined, and compared with those obtained in OMV vaccinated mice.

Alternative Approaches to Vaccine Delivery by OMVs

OMVs from pathogenic and commensal bacteria survive intact GI-transit and can penetrate the intestinal epithelium, access mucosal APCs and activate immune cells (Collins, 2011 and Van der Pol et al., 2015). If Bt OMV vaccine-mediated immune cell responses are weaker than those generated by pathogenic and commensal bacterial OMVs, OMV immunogenicity is improved by increasing expression levels of the vaccine Ag using alternate secretory signal sequences, selecting size fractionated populations of OMVs expressing the highest levels of the vaccine Ag or by co-expressing vaccine Ag in the same OMV preparation. OMV surface-associated proteins can be significantly resistant to protease treatment (Ohta et al., 1993), but if a particular protein is shown to be susceptible to intestinal proteases an intranasal route of delivery is selected, which can generate protective immunity using pathogen-derived OMVs (Van der Pol et al., 2015).

Demonstration of Vaccination by Bt OMV in Other Species

The success of the mouse model for Bt OMV vaccination provides the rationale for testing Bt OMV vaccines in animals and humans. The logical disease and target populations are *salmonellosis* in farm animals (pigs and chickens) and norovirus infection in vulnerable and at risk human populations. For example, transgenic chickens expressing CSF1R-reporter genes (MacRed and MacGreen chickens) (Balic et al., 2014) are used to optimise avian OMV vaccination protocols.

Example D—Demonstration of Effectiveness of OMVs for Delivery of a Therapeutic Polypeptide Treatment with OMVs Containing Expressed KGF-2 Reduces the Pathology of Induced Colitis in the Mouse in a Chemically Induced Model of Colitis (FIG. 8).

*B. thetaiotaomicron* cells were engineered to express and secrete recombinant human keratinocyte growth factor-2 (KGF-2; Fibroblast growth factor-10; FGF-10; UniprotKB 015520) fused to the N-terminal signal peptide of OmpA of Bt (BT_3852) in OMVs. Amino acid residues 38-208 of the KGF-2 sequence (the full length protein minus its signal peptide) was fused at its N-terminus to the *B. thetaiotaomicron* signal peptide of OmpA (BT_3852; UniprotKB Q8A119), the amino acid sequence of which is MKKILMLLAFAGVASVASA. The fused product was cloned into the expression vector pGH90 (Wegmann et al., 2013), resulting in the production of pGH173 (See FIG. 9). OMVs were prepared according to the methods of Stentz et al., 2015, and Stentz et al., 2014, and as described in Example B above. Polyclonal goat biotinylated anti-human FGF-10 (KGF-2) antibodies (PeproTech) were used in immunoblotting to detect the presence of the recombinant protein in OMV lysates. The mouse model for colitis was produced by administration of 2.5% dextran sulfate sodium (DSS) to adult mice via drinking water for 7 days. DSS-administered mice were gavaged at days 1, 3 and 5 with either (i) PBS containing 2.5% DSS (DSS-PBS), (ii) control OMVs suspended in 2.5% DSS (DSS-OMV) or (iii) OMVs containing recombinant KGF-2 suspended in 2.5% DSS (DSS-OMVKGF). Control mice (no DSS administration) were similarly gavaged at days 1, 3 and 5 with either (i) PBS (H2O-PBS), (ii) control OMV (H2O OMV) or (iii) OMV containing recombinant KGF-2 (H2O-OMVKGF). n=5 for all treatments. Disease activity index (DAI) scores (Hamady et al., 2010) were assessed for all mice, based on cumulative scores for weight loss, colon content consistency and colon content blood and appearance of caecum and colon tissue presented at day 7. Colonic length was measured from the ileocaecal junction to the anal verge at necropsy. Body weight loss was calculated as the percentage of the weight at day 7 over day 0.

As can be seen from FIG. 8, treatment with OMVs containing expressed recombinant KGF-2 significantly improved the DAI scores, reduction in colon length and weight loss seen in DSS-administered mice, as compared to control mice ($p<0.05$ significantly different from the control group receiving the same treatment (PBS, OMV or OMV-KGF), One way Anova). Treatment with OMVs containing expressed recombinant KGF-2 had no significant deleterious effects on control (non-DSS administered) mice when compared to PBS or control OMV treatment.

TABLE

S1. List of bacterial strains and plasmids used in this study.

| Species | Strain | Plasmid | Promoter | Genome region | RBS | Overexpressed gene | Antibiotic selection | Reference |
|---|---|---|---|---|---|---|---|---|
| *E. coli* | GH019 | pGH001 | P1 | | low | pepI | Amp | (1) |
| JM109 | GH079 | pGH020 | P1 | | med | | Amp | (1) |
| | GH081 | pGH022 | PI | | med | pepI | Amp | (1) |
| | GH188 | pGH063 | | | med | pepI | Amp Tet | This study |
| | GH303 | pGH117 | P3784 | | med | | Amp Ery | This study |
| | GH317 | pGH122 | P3784 | | low | | Amp Ery | This study |
| | GH349 | pGH141 | P3784 | | low | | Amp Ery | This study |
| | GH350 | pGH142 | P3784 | | med | | Amp Ery | This study |
| | GH405 | pGH125med | P3784 | | med | | Amp Ery | This study |
| *B. thetaiotaomicron* | Bt VPI 5482 | | | | | | | |
| VPI-5482 | GH221[a] | | | | | | Tet | |
| | GH189 | pGH022 | P1 | | med | pepI | Tet | (1) this study |
| | GH190 | pGH063 | | | med | pepI | Tet | This study |
| | GH193 | pGH066 | P3784 | 4912647-4912919 | med | pepI | Tet | This study |
| | GH287 | pGH105 | P3784 | 4912647-4912919 | low | pepI | Tet | This study |
| | GH288 | pGH106 | P3784 | 4912647-4912919 | med | | Tet | This study |
| | GH289 | pGH107 | P3784 | 4912647-4912919 | low | | Tet | This study |
| | GH359 | pGH117 | P3784 | 4912647-4912919 | med | | Tet | This study |
| | GH360 | pGH122 | P3784 | 4912647-4912919 | low | | Ery | This study |
| | GH361 [a] | pGH141 | P3784 | 4912647-4912919 | low | BtcepA | Ery | This study |
| | GH364 [a] | pGH142 | P3784 | 4912647-4912919 | med | BtcepA | Ery | This study |
| | GH402 [a] | pGH150 | P3784 | 4912647-4912919 | med | BtcepA[His]$_4$ | Ery | This study |

[a] *B. thetaiotaomicron* ΔBtcepA strain

TABLE 2

Table S2. Oligonucleotide primers used in this study.

| Name | SEQ ID NO. | Sequence* |
|---|---|---|
| f-noPpepI | [SEQ ID NO. 4] | ATATA*GCATGCCCATGGCTCGAGAAAAGCGCT*CCATATAAAGACACCATGC |
| r-ppepI/NotI | [SEQ ID NO. 5] | ATGACCTGGCG*GCCGC* |
| f-3784_3786 | [SEQ ID NO. 6] | ACCGCACCTCCAATAAATAACAGG |
| r-3784_3786_sp | [SEQ ID NO. 7] | TGACGCATGCAATGTTTTTTCATGGCATAGAATCC |
| f-RSS$_{law}$-pepI | [SEQ ID NO. 8] | **ATTATAAGGAGGCACTCACCAT**GCAAATCACAGAAAAATATCTTCC |

TABLE 2-continued

| Table S2. Oligonucleotide primers used in this study. | | |
|---|---|---|
| Name | SEQ ID NO. | Sequence* |
| f-3784_RBS$_{law}$ | [SEQ ID NO. 9] | **ATGGTGAGTGCCTCCTTATAAT**ACCGCACCTAATAAATAAATAACAGG |
| f-RBS$_{med}$_MCS | [SEQ ID NO. 10] | AGTACCATGGTGTCTTTTCTTTTATATGG |
| f-RBS$_{law}$_MCS | [SEQ ID NO. 11] | AGTACCCATGGTGAGTGCCTCCTTATATAATACCGCACCTCCAATAAATAACAGG |
| ccR_amont2 | [SEQ ID NO. 12] | CATGCATATGAGCTCCATGCTATAGCTACC |
| ccR_aval2 | [SEQ ID NO. 13] | CATGGGATCCGCCAGCCGTTATGCGGCAGC |
| Tev-His6_linker_5' | [SEQ ID NO. 14] | CATGGAGGCCTGAGAACCTGTACTTCCAATCCGCTGGACACCACCATCATCATCATTAACCC |
| Tev-His6_linker_3' | [SEQ ID NO. 15] | GGGTTAATGATGATGATGGTGGTGTCCAGCGGATTGGAGTACAGGTTCTCAGGCCTC |
| Lactamase_F | [SEQ ID NO. 16] | CGCTCATTCATCCTGCTTC |
| Lactamase_EcoRI_R | [SEQ ID NO. 17] | ATATG*AATTC*TTATTGATGCGTCACA |
| B-Lact_nostop_R | [SEQ ID NO. 18] | TTGATGCGTCACATATTCG |

*The underlined sequence regions match their template. The sequence in italics shows restriction endonuclease recognition sequences. The sequence parts in bold designate the overlap in the splicing by overlap extension PCR.

TABLE 3

| BDM adapted (BDMA) composition | |
|---|---|
| Base medium | Final concentration |
| Potassium phosphate (pH7.4) | 100 mM |
| (NH4)2SO4 | 8.3 mM |
| Hemin | 0.01% |
| Histidine | 0.2 mM |
| Casitone | 0.2% |
| L-cysteine | 4.1 mM |
| Sugar | 0.5% |
| Mineral solution | 0.61 ml/L |
| Vitamin solution | 0.61 ml/L |
| **Mineral solution** | **g/L** |
| NaCl | 18 |
| $MgCl_2$ | 0.4 |
| $CaCl_2$ | 0.4 |
| $MnCl_2 \cdot 4H_2O$ | 0.2 |
| $CoCl_2 \cdot 6H_2O$ | 0.02 |
| **Vitamin solution** | **mg/L** |
| Biotin | 16.4 |
| Cobalanine (Vit B12) | 16.4 |
| p-ou-4-aminobenzoic acid | 49.1 |
| Folic acid | 82 |
| pyridoxamine dihydrochloride | 246 |
| Thiamine | 82 |
| Riboflavine | 82 |

TABLE 4

| BiCepA β-lactamase activity after mannan induction | | | | |
|---|---|---|---|---|
| Strain | Description | Mannan (mg/l) | nmol/mg/min | Fold-Induction[b] |
| GH359 | WT ($P_{3784}$_low) | 0 | 304.5 ± 41.3 | — |
| | | 0 [$Cef_5$][a] | 642.9 ± 70.9 | — |
| GH360 | ΔBtcepA ($P_{3784}$_low) | 50 | 3.4 ± 2.0 | — |
| GH361 | ΔBtcepA ($P_{3784}$_low::BtcepA) | 0 | 11.4 ± 0.3 | 1.0 |
| | | 50 | 131.7 ± 4.6 | 11.6 |
| | | 100 | 177.1 ± 26.9 | 15.6 |
| | | 250 | 191.1 ± 25.5 | 16.8 |
| GH364 | ΔBtcepA ($P_{3784}$_med::BtcepA) | 0 | 1016.9 ± 13.4 | 89.4 |
| | | 5 | 5872.3 ± 350.4 | 516.4 |
| | | 50 | 13133.2 ± 503.7 | 1154.9 |

[a]Addition of 5 mg/l cefotaxime

[b]Induction factor = the mean value obtained in the indicated conditions/the mean value obtained for the non-induced GH361 strain (11.4).

REFERENCES

Alaniz, et al., *J Immunol,* 2007, 179:7692-7701.
Arvidsson et al., *J. Antimicrob. Chemother,* 1982, 10:207-15.
Balic, et al., *Development,* 2014, 141:3255-65.
Ball, et al., *Gastroenterology,* 1999, 117:40-48.
Bayley, et al., *FEMS Microbiol Lett,* 2000, 193:149-54.
Berlanda Scorza, et al., *Mol Cell Proteom,* 2008, 7:473-85.
Bernstein, et al., *J Infect Dis,* 2015, 211:870-8.
Bradford, et al., *Immunobiol,* 2011, 216:1228-1237.
Bumann, *Front Immunol,* 2014, 5:381-9.
Cerovic, et al., *Mucosal Immunol,* 2013, 6:104-113.
Chionh, et al., *Gut Microbes,* 2010, 1:42-44.
Collins, *Discov Med,* 2011, 62:7-15.
Cuskin et al., *Nature,* 2015, 517: 165-9.
Degnan and Macfarlane, *Anaerobe,* 1995, 1:25-33.
Desai, et al., *Clin Infect Dis,* 2012, 55:189-193.
Donaldson, et al., *Immunol,* 2012, 137:131-131.
Donaldson, et al., *J Virol,* 2015, 89:9532-9547.
Düsterhöft et al., *J. Sci. Food Agr,* 1993, 63:211-220.
Elam-Evans, et al., *MMWR,* 2104, 63:741-748.
El-Kamary, et al., *J Infect Dis,* 2010, 202:1649-1658.
Foxwell, et al., *Hum Vaccines,* 2007, 3:220-223.
Gardiner, et al., *J Extracell Vesicles,* 2013, 2:19671.

Gil-Cruz, et al., *PNAS USA,* 2009, 106:9803-9808.
Hall, et al., *Emerg. Infect. Dis.,* 2013, 19:1305-1309.
Hamady et al., *Microbiology,* 2008, 154:3165-74.
Hamady, et al., *Gut,* 2010, 59:461-9.
Hamady, et al., *Inflammatory bowel diseases,* 2011, 17:1925-35.
Hase, et al., *Nature,* 2009, 462:226-232.
Hickey, et al., *Cell Host Microbe,* 2015, 17:672-80.
Hoft, et al., *Cell Microbio,* 2011, 13:934-942.
Houston, et al., *Mucosal Immunol,* 2015, In Press.
Huang et al., *Z Naturforsch C,* 2010, 65:387-90.
Kanaya, et al., *Nat Immunol,* 2012, 13:729-734.
Kang, et al., *PloS One,* 2013, 8:e76520.
Kaparakis-Liaskos, et al., *Nature Revs Immunol,* 2015, 15:375-87.
Kesty, et al., *J Biol Chem,* 2004, 279:2069-2076.
Kim, et al., *Exp Mol Med,* 2014, 46:e85.
Kimura, et al., *Mucosal Immunol,* 2015, 8:650-660.
Kingsley, et al., *Mol Microbiol,* 2004a, 52:345-355.
Kingsley, et al., *Mol Microbiol,* 2002, 43:895-905.
Kingsley, et al., *J Bacteriol,* 2004b, 186:4931-4939
Klein et al., Microbiology, 1994, 140:1133-9.
Knoop, et al., *J Immunol,* 2009, 183:5738-5747.
Kobayashi, et al., *Mucosal Immunol,* 2013, 6:1027-1037.
Lee, et al., *Plos Pathog,* 2012, 8:e1002499.
Lee, *Proteomics,* 2007, 7:3821-3821.
Lewison, 1997, Gastroenterology in the UK: The burden of disease (Brit. Soc. Gastro. and Brit. Digest. Found. Report).
Lindesmith, et al., *Open Forum Infect Dis,* 2015, 2:1-8.
Mabbott, et al., *Mucosal Immunol,* 2013, 6:666-677.
Martens et al., *Cell Host Microbe,* 2008, 4:447-57.
Martens et al., *J. Biol. Chem.,* 2009, 284:18445-57.
Martens et al., *PLoS Biol,* 2011, 9: e1001221.
Mastroeni, et al., *Microbes Infect,* 2004, 6:398-405.
McBroom, et al., *J Bacteriol,* 2006, 188:5385-5392.
McBroom, et al., *Mol Microbiol,* 2007, 63:545-558.
Mimee et al., *Cell Syst,* 2015, 1: 62-711.
Mutoh, et al., *Cell Tissue Res.,* 2015, 57:39-43.
Nakato, et al., *J Immunol,* 2012, 189:1540-1544.
Nauciel, *J Immunol.,* 2000, 145:1265-1269.
NOAH. Vaccination of farm animals. 2014: http://www.noah.co.uk/issues/vaccines.htm.
Ohta, et al., *Infect Immun,* 1993, 61:4878-4884.
Parker and Jeffrey Smith, 2012, *Plasmid,* 68:86-92.
Powell, et al., *Nat Nanotechnol,* 2015, 10:361-369.
Reynolds, et al., *Immunol,* 2014, 143:438-446.
Rios, et al., *Mucosal Immunol,* 2015, In Press:doi: 10.1038/mi.2015.121.
Rollenhagen, et al., *PNAS USA,* 2004, 101:8739-8744. Salyers, et al., *Appl. Environ. Microbiol,* 1977, 33:319-22.
Sambrook, Molecular cloning: a Laboratory Manual, 2001, New-York USA.
Sasmono, et al., *J Leukocyte Biol,* 2007, 82:111-123.
Sauter, et al., *PloS One,* 2014, 9:e105429.
Shima, et al., *Int Immunol,* 2014, 26:619-625.
Shoemaker et al., *Bacteriol,* 1986, 165: 929-36.
Smith et al., *Plasmid,* 1995, 34:211-22.
Sonnenburg et al., *Proc Natl Acad Sci USA,* 2006, 103:8834-9.
Sonnenburg et., *Cell,* 2010, 141, :1241-52.
Soo, et al., *Immunol,* 2012, 136:192-7.
Stentz et al., *J. Antimicrob. Chemother,* 2015, 70:701-9.
Stentz, et al., *Cell Reports,* 2014, 6:646-56.
Strobel and Russel, *Appl. Environ. Microbiol,* 1987, 53:2505-10.
Tacket, et al., *Clin Immunol,* 2003, 108:241-247.
Tam, et al., 2011, The IID2 study (FSA Report).
Trivedi, et al., *Am J Infect Control,* 2013, 41:654-657.
Ulmer, et al., *Nat Biotechnol,* 2006, 24:1377-1383.
Van der Pol, et al., *Biotech. J.,* 2015, 10:1689-1706.
Verhoef, et al., *Emerg Infect Dis,* 2010, 16:617-624.
Vingadassalom, et al., *Mol. Microbiol,* 2005, 56:888-902.
Voehringer, et al., *Blood,* 2002, 100:3698-3702.
Wang, et al., *J Immunol,* 2011, 187:5277-85.
Wang, et al., *Microb Pathogenesis,* 2013, 58:17-28.
Wegmann, et al., *Appl Environ Microb,* 2013, 79:1980-1989.
Withanage, et al., *Infect Immun,* 2005, 73:5173-5182.
Xu et al., *Science,* 2003, 299: 2074-6

The invention claimed is:

1. A recombinant gram negative commensal gut bacterium from the *Bacteroides* genus comprising an expression system for expression of a heterologous peptide or protein, wherein said heterologous peptide or protein is contained in an outer membrane vesicle (OMV), characterised in that the heterologous peptide or protein is fused to the N-terminal signal peptide of the OMV-secreted protein Bt OmpA.

2. A recombinant gram negative commensal gut bacterium as claimed in claim 1 wherein the heterologous peptide or protein is a therapeutic peptide, a therapeutic protein or an antigen.

3. A recombinant gram negative commensal gut bacterium as claimed in claim 1 wherein the expression system is a mannan-controlled inducible gene expression system.

4. A recombinant gram negative commensal gut bacterium as claimed in claim 3 wherein the inducible gene expression system comprises:

a mannan-inducible promoter region of an alpha-1,2-mannosidase gene;

at least one ribosomal binding site;

a multiple cloning site; and a transcriptional terminator.

5. A method for preparing an outer membrane vesicle (OMV) containing a heterologous peptide or protein within the OMV, comprising generating a recombinant gram negative commensal gut bacterium from the *Bacteroides* genus that expresses a heterologous peptide or protein fused to the N-terminal signal peptide of the OMV-secreted protein Bt OmpA, BtMinpp or BtCepA, cultivating the bacterium under conditions that result in the expression of said heterologous peptide or protein and the production of OMV, and isolating OMV thereby containing said heterologous peptide or protein.

6. A method as claimed in claim 5 wherein expression of the heterologous peptide or protein is mannan-inducible.

7. A method as claimed in claim 6 wherein induction of the expression of the heterologous peptide or protein is delayed until OMV production.

8. A method as claimed in claim 7 wherein induction of the expression of the heterologous peptide or protein is tuned using varying concentrations of mannan.

9. A recombinant gram negative commensal gut bacterium as claimed in claim 1 wherein the recombinant gram negative commensal gut bacterium is *Bacteroides thetaiotaomicron* (Bt).

10. A recombinant gram negative commensal gut bacterium from the *Bacteroides* genus comprising an expression system for expression of a heterologous peptide or protein within an outer membrane vesicle (OMV), characterised in that the heterologous peptide or protein is fused to the N-terminal signal peptide of an OMV secreted protein.

11. A recombinant gram negative commensal gut bacterium as claimed in claim 10 wherein the heterologous peptide or protein is fused to the N-terminal signal peptide of the OMV-secreted protein Bt OmpA.

12. A recombinant gram negative commensal gut bacterium from the *Bacteroides* genus comprising an expression system for expression of a heterologous peptide or protein, wherein said heterologous peptide or protein is contained in an outer membrane vesicle (OMV), characterised in that the heterologous peptide or protein is fused to the N-terminal signal peptide of the OMV-secreted protein BtMinpp.

13. A recombinant gram negative commensal gut bacterium from the *Bacteroides* genus comprising an expression system for expression of a heterologous peptide or protein, wherein said heterologous peptide or protein is contained in an outer membrane vesicle (OMV), characterised in that the heterologous peptide or protein is fused to the N-terminal signal peptide of the OMV-secreted protein BtCepA.

* * * * *

SEQUENCE LISTING

```
<160> NUMBER OF SEQ ID NOS: 18

<210> SEQ ID NO 1
<211> LENGTH: 19
<212> TYPE: PRT
<213> ORGANISM: Bacteroides thetaiotaomicron

<400> SEQUENCE: 1

Met Lys Lys Ile Leu Met Leu Leu Ala Phe Ala Gly Val Ala Ser Val
1               5                   10                  15

Ala Ser Ala


<210> SEQ ID NO 2
<211> LENGTH: 272
<212> TYPE: DNA
<213> ORGANISM: Bacteroides thetaiotaomicron

<400> SEQUENCE: 2

aatgtttttt catggcatag aatccttaga tttgcaatat gacaaaggta aacaaaaaaa      60

ctttccagca cttttttggc gcagaatata tgtaagaatg cgtgccagtt tggttaatta     120

tagcgccaca gggcgattta gtgtttcgac ttccggtagc ggcattcctt ttctctctat     180
```

-continued tttcgtcaca gaaactaatt ttattcataa attcatttgt tcatgaaaac acatttttca 240
tttaaacacc tgttatttat tggaggtgcg gt 272

<210> SEQ ID NO 3
<211> LENGTH: 41
<212> TYPE: DNA
<213> ORGANISM: Bacteroides thetaiotaomicron

<400> SEQUENCE: 3 actttttgg cgcagaatat atgtaagaat gcgtgccagt t 41

<210> SEQ ID NO 4
<211> LENGTH: 59
<212> TYPE: DNA
<213> ORGANISM: Artificial Sequence
<220> FEATURE:
<223> OTHER INFORMATION: f-noPpepI Oligonucleotide primer

<400> SEQUENCE: 4
atatatgcat gcccatggct cgagaaaagc gctcccatat aaaagaaaag acaccatgc 59

<210> SEQ ID NO 5
<211> LENGTH: 16
<212> TYPE: DNA
<213> ORGANISM: Artificial Sequence
<220> FEATURE:
<223> OTHER INFORMATION: r-ppepI/NotI Oligonucleotide primer

<400> SEQUENCE: 5
atgacctggc ggccgc 16

<210> SEQ ID NO 6
<211> LENGTH: 24
<212> TYPE: DNA
<213> ORGANISM: Artificial Sequence
<220> FEATURE:
<223> OTHER INFORMATION: f-3784_3786 Oligonucleotide primer

<400> SEQUENCE: 6
accgcacctc caataaataa cagg 24

<210> SEQ ID NO 7
<211> LENGTH: 35
<212> TYPE: DNA
<213> ORGANISM: Artificial Sequence
<220> FEATURE:
<223> OTHER INFORMATION: r-3784_3786_sp Oligonucleotide primer

<400> SEQUENCE: 7
tgacgcatgc aatgtttttt catggcatag aatcc 35

<210> SEQ ID NO 8
<211> LENGTH: 46
<212> TYPE: DNA
<213> ORGANISM: Artificial Sequence
<220> FEATURE:
<223> OTHER INFORMATION: f-RSSlaw-pepI Oligonucleotide primer

<400> SEQUENCE: 8
attataagga ggcactcacc atgcaaatca cagaaaaata tcttcc 46

<210> SEQ ID NO 9
<211> LENGTH: 48
<212> TYPE: DNA
<213> ORGANISM: Artificial Sequence
<220> FEATURE:
<223> OTHER INFORMATION: f-3784_RBSlaw Oligonucleotide primer

<400> SEQUENCE: 9
atggtgagtg cctccttata ataccgcacc taataaataa ataacagg 48

<210> SEQ ID NO 10
<211> LENGTH: 29
<212> TYPE: DNA
<213> ORGANISM: Artificial Sequence
<220> FEATURE:
<223> OTHER INFORMATION: f-RBSmed_MCS Oligonucleotide primer

<400> SEQUENCE: 10
agtaccatgg tgtcttttct tttatatgg 29

<210> SEQ ID NO 11
<211> LENGTH: 55
<212> TYPE: DNA
<213> ORGANISM: Artificial Sequence
<220> FEATURE:
<223> OTHER INFORMATION: f-RBSlaw_MCS Oligonucleotide primer

<400> SEQUENCE: 11
agtacccatg gtgagtgcct ccttatataa taccgcacct ccaataaata acagg 55

<210> SEQ ID NO 12
<211> LENGTH: 30
<212> TYPE: DNA
<213> ORGANISM: Artificial Sequence
<220> FEATURE:
<223> OTHER INFORMATION: ccR_amont2 Oligonucleotide primer

<400> SEQUENCE: 12
catgcatatg agctccatgc tatagctacc 30

<210> SEQ ID NO 13
<211> LENGTH: 30
<212> TYPE: DNA
<213> ORGANISM: Artificial Sequence
<220> FEATURE:
<223> OTHER INFORMATION: ccR_aval2 Oligonucleotide primer

<400> SEQUENCE: 13
catgggatcc gccagccgtt atgcggcagc 30

<210> SEQ ID NO 14
<211> LENGTH: 62
<212> TYPE: DNA
<213> ORGANISM: Artificial Sequence
<220> FEATURE:
<223> OTHER INFORMATION: Tev-His6_linker_5? Oligonucleotide primer

<400> SEQUENCE: 14
catggaggcc tgagaacctg tacttccaat ccgctggaca ccaccatcat catcattaac 60
cc 62

<210> SEQ ID NO 15
<211> LENGTH: 57
<212> TYPE: DNA
<213> ORGANISM: Artificial Sequence
<220> FEATURE:
<223> OTHER INFORMATION: Tev-His6_linker_3? Oligonucleotide primer

<400> SEQUENCE: 15

-continued

```
gggttaatga tgatgatggt ggtgtccagc ggattggagt acaggttctc aggcctc        57


<210> SEQ ID NO 16
<211> LENGTH: 19
<212> TYPE: DNA
<213> ORGANISM: Artificial Sequence
<220> FEATURE:
<223> OTHER INFORMATION: Lactamase_F Oligonucleotide primer

<400> SEQUENCE: 16

cgctcattca tcctgcttc                                                  19


<210> SEQ ID NO 17
<211> LENGTH: 26
<212> TYPE: DNA
<213> ORGANISM: Artificial Sequence
<220> FEATURE:
<223> OTHER INFORMATION: Lactamase_EcoRI_R Oligonucleotide primer

<400> SEQUENCE: 17

atatgaattc ttattgatgc gtcaca                                          26


<210> SEQ ID NO 18
<211> LENGTH: 19
<212> TYPE: DNA
<213> ORGANISM: Artificial Sequence
<220> FEATURE:
<223> OTHER INFORMATION: B-Lact_nostop_R Oligonucleotide primer

<400> SEQUENCE: 18

ttgatgcgtc acatattcg                                                  19
```